US009169310B2

(12) United States Patent
Riber et al.

(10) Patent No.: US 9,169,310 B2
(45) Date of Patent: Oct. 27, 2015

(54) GLUCAGON ANALOGUES

(75) Inventors: Ditte Riber, Brønshøj (DK); Eddi Meier, Vaerløse (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 13/704,299

(22) PCT Filed: Jun. 24, 2011

(86) PCT No.: PCT/DK2011/000072
§ 371 (c)(1),
(2), (4) Date: Mar. 6, 2013

(87) PCT Pub. No.: WO2011/160633
PCT Pub. Date: Dec. 29, 2011

(65) Prior Publication Data
US 2013/0157929 A1    Jun. 20, 2013

Related U.S. Application Data

(60) Provisional application No. 61/358,614, filed on Jun. 25, 2010.

(30) Foreign Application Priority Data

Jun. 24, 2010  (DK) ................. 2010 00558

(51) Int. Cl.
*A61K 38/26*   (2006.01)
*A61K 45/06*   (2006.01)
*C07K 14/605*  (2006.01)

(52) U.S. Cl.
CPC ............. *C07K 14/605* (2013.01); *A61K 38/26* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,994,122 | B2 | 8/2011 | Riber et al. |
| 8,642,540 | B2 | 2/2014 | Meier et al. |
| 8,642,541 | B2 | 2/2014 | Meier et al. |
| 8,680,049 | B2 | 3/2014 | Meier et al. |
| 8,685,919 | B2 | 4/2014 | Meier et al. |
| 2005/0070469 | A1 | 3/2005 | Bloom et al. |
| 2010/0099601 | A1 | 4/2010 | Weiss |
| 2010/0190701 | A1 | 7/2010 | Day et al. |
| 2011/0286981 | A1 | 11/2011 | Meier et al. |
| 2011/0286982 | A1 | 11/2011 | Meier et al. |
| 2011/0293586 | A1 | 12/2011 | Meier et al. |
| 2011/0293587 | A1 | 12/2011 | Meier et al. |
| 2012/0178670 | A1 | 7/2012 | Riber et al. |
| 2013/0157929 | A1 | 6/2013 | Riber et al. |
| 2013/0157935 | A1 | 6/2013 | Meier et al. |
| 2013/0157953 | A1 | 6/2013 | Petersen et al. |
| 2013/0316941 | A1 | 11/2013 | Hamprecht et al. |
| 2014/0011733 | A1 | 1/2014 | Fosgerau et al. |
| 2014/0080757 | A1 | 3/2014 | Tolborg et al. |
| 2014/0127174 | A1 | 5/2014 | Meier et al. |
| 2014/0127175 | A1 | 5/2014 | Meier et al. |
| 2015/0080295 | A1 | 3/2015 | Meier et al. |
| 2015/0111817 | A1 | 4/2015 | Riber et al. |
| 2015/0111826 | A1 | 4/2015 | Riber et al. |

FOREIGN PATENT DOCUMENTS

| | | |
|---|---|---|
| AU | 2008326324 A1 | 5/2009 |
| CN | 101519446 A | 9/2009 |
| DE | 102008003566 A1 | 7/2009 |
| DE | 102008003568 A1 | 7/2009 |
| EP | 0082731 A1 | 6/1983 |
| EP | 2025684 A1 | 2/2009 |
| WO | WO-98/08871 A1 | 3/1998 |
| WO | WO-98/11125 A1 | 3/1998 |
| WO | WO-98/11126 A1 | 3/1998 |
| WO | WO-99/25727 A2 | 5/1999 |
| WO | WO-99/46283 A1 | 9/1999 |
| WO | WO-00/34331 A2 | 6/2000 |
| WO | WO-00/55119 A1 | 9/2000 |
| WO | WO-00/55184 A1 | 9/2000 |
| WO | WO-01/04156 A1 | 1/2001 |
| WO | WO-03/022304 A1 | 3/2003 |
| WO | WO-03/053339 A2 | 7/2003 |
| WO | WO-03/053460 A1 | 7/2003 |
| WO | WO-2004/062685 A2 | 7/2004 |
| WO | WO-2004/096854 A2 | 11/2004 |
| WO | WO-2006/134340 A2 | 12/2006 |
| WO | WO-2007/024899 A2 | 3/2007 |
| WO | WO-2007/056362 A2 | 5/2007 |
| WO | WO-2007/081824 A2 | 7/2007 |

(Continued)

OTHER PUBLICATIONS

Abbrecht et al., "Erythrocyte life-span in mice acclimatized to different degrees of hypoxia," *J. Appl. Physiol.* 32:443-445, 1972.
Adelhorst et al., "Structure-activity studies of glucagon-like peptide-1," *J. Biol. Chem.* 269:6275-6278, 1994.
Altschul et al., "Local Alignment Statistics," *Methods in Enzymology* 266:460-480, 1996.
Authier et al., "Endosomal Proteolysis of Glucagon at Neutral pH generates the bioactive Degradation Product Miniglucagon-(19-29)," *Endocrinology* 144:5353-5364, 2003.
Blache et al., "Endopeptidase from Rat Liver Membranes, Which Generates Miniglucagon from Glucagon," *J. Biol. Chem.* 268:21748-21753, 1993.
Cavanaugh et al., "Isolation and Structural Characterization of Proglucagon-Derived Peptides, Pancreatic Polypeptide, and Somatostatin from the Urodele *Amphiuma tridactylum*," *Gen. Compar. Endocrin.* 101:12-20, 1996.

(Continued)

*Primary Examiner* — Thomas S Heard
(74) *Attorney, Agent, or Firm* — Clark & Elbing LLP; Kristina Bieker-Brady

(57) ABSTRACT

The invention provides materials and methods for promoting weight loss or preventing weight gain and for treating diabetes and associated metabolic disorders. In particular, the invention provides novel glucagon analogue peptide compounds effective in such methods. The compounds may mediate their effect by having, for example, increased selectivity for the GLP-1 receptor compared to human glucagon.

17 Claims, No Drawings

(56) References Cited

FOREIGN PATENT DOCUMENTS

| | | |
|---|---|---|
| WO | WO-2007/100535 A2 | 9/2007 |
| WO | WO-2008/010101 A2 | 1/2008 |
| WO | WO-2008/071972 A1 | 6/2008 |
| WO | WO-2008/101017 A2 | 8/2008 |
| WO | WO-2008/152403 A1 | 12/2008 |
| WO | WO-2009/067636 A2 | 5/2009 |
| WO | WO-2009/087081 A2 | 7/2009 |
| WO | WO-2009/087082 A2 | 7/2009 |
| WO | WO-2009/129250 A2 | 10/2009 |
| WO | WO-2009/132129 A2 | 10/2009 |
| WO | WO-2009/152128 A1 | 12/2009 |
| WO | WO-2009/155257 A1 | 12/2009 |
| WO | WO-2009/155258 A2 | 12/2009 |
| WO | WO-2010/002283 A9 | 1/2010 |
| WO | WO-2010/014946 A2 | 2/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010/080606 A1 | 7/2010 |
| WO | WO-2010/080609 A1 | 7/2010 |
| WO | WO-2011/006497 A1 | 1/2011 |
| WO | WO-2011/088837 A1 | 7/2011 |
| WO | WO-2011/160630 A2 | 12/2011 |
| WO | WO-2011/160633 A1 | 12/2011 |
| WO | WO-2012/098462 A1 | 7/2012 |
| WO | WO-2013/092703 A2 | 6/2013 |
| WO | WO-2014/041195 A1 | 3/2014 |

OTHER PUBLICATIONS

Chan et al., "Suppression of weight gain by glucagon in obese Zucker rats," *Exp. Mol. Path.* 40:320-327, 1984.
Cohen et al., "Oxyntomodulin Suppresses Appetite and Reduces Food Intake in Humans," *Journal of Clinical Endocrinology & Metabolism* 88:4696-4701, 2003.
Dakin et al., "Oxyntomodulin Inhibits Food Intake in the Rat," *Endocrinology* 142:4244-4250, 2001.
Dakin et al., "Peripheral oxyntomodulin reduces food intake and body weight gain in rats," *Endocrinology* 145:2687-2695, 2004.
Day et al., "A new glucagon and GLP-1 co-agonist eliminates obesity in rodents," *Nat. Chem. Biol.* 5:749-757, 2009.
Delgado et al., "The uses and properties of PEG-linked proteins," *Crit. Rev. Ther. Drug. Carrier Syst.* 9:249-304, 1992.
Druce et al., "Investigation of structure-activity relationships of Oxyntomodulin (Oxm) using Oxm analogs," *Endocrinology* 150:1712-1721, 2009.
England et al., "Glucagon Carboxyl-Terminal Derivatives: Preparation, Purification and Characterization," *Biochemistry* 21:940-950, 1982.
Francis et al., "PEGylation of cytokines and other therapeutic proteins and peptides: the importance of biological optimisation of coupling techniques," *Int. J. Hematol.* 68:1-18, 1998.
Frandsen et al., "Glucagon: Structure-Function Relationships Investigated by Sequence Deletions," *Hoppe-Seyler's Z. Physiol. Chem.* 362:665-677, 1981.
Gelfanov et al., "Discovery and structural optimization of high affinity co-agonists at the glucagon and GLP-1 receptors," *Understanding Biology Using Peptides*, ed. Sylvie E. Blondelle, American Peptide Society, 763-764, 2005.
Göke et al.,"Exendin-4 is a high potency agonist and truncated exendin-(9-39)-amide an antagonist at the glucagon-like peptide 1-(7-36)-amide receptor of insulin-secreting β-cells," *J. Biol. Chem.* 268:19650-19655, 1993.
Gombotz et al. "Biodegradable Polymers for Protein and Peptide Drug Delivery," *Bioconjugate Chem.* 6:332-351, 1995.
Hjorth et al., "Glucagon and Glucagon-Like Peptide 1: Selective Receptor Recognition Via Distinct Peptide Epitopes," *J. Biol. Chem.* 269:30121-30124, 1994.
Hruby et al., "The design and biological activities of glucagon agonists and antagonists, and their use in examining the mechanisms of glucose action," *Curr. Med. Chem.—Imm., Endoc. & Metab. Agents* 1:199-215, 2001.
Hudecz et al., "Synthesis, Conformation, Biodistribution, and in Vitro Cytotoxicity of Daunomycin-Branched Polypeptide Conjugates," *Bioconjugate Chem.* 3:49-57, 1992.
International Search Report for PCT/DK2011/000072, mailed Dec. 6, 2011 (3 pages).
Joshi et al., "The Estimation of Glutaminyl Deamidation and Aspartyl Cleavage Rates in Glucagon," *Int. J. Pharma.* 273:213-219, 2004.
Kallenbach et al., "Role of the Peptide Bond in Protein Structure and Folding." *The Amide Linkage*, Chapter 18, pp. 599-622, 2000.
Knudsen et al., "Potent Derivatives of Glucagon-like Peptide-1 with Pharmacokinetic Properties Suitable for Once Daily Administration," *J. Med. Chem.* 43:1664-1669, 2000.
Madsen et al., "Structure-activity and protraction relationship of long-acting glucagon-like peptide-1 derivatives: importance of fatty acid length, polarity, and bulkiness," *J. Med. Chem* 50:6126-6132, 2007.
McKee et al., "Receptor binding and adenylate cyclase activities of glucagon analogues modified in the N-terminal region," *Biochemistry* 25:1650-1656, 1986.
NCBI Genbank Accession No. 721913A, downloaded Dec. 15, 2009.
Pan et al, "Design of a long acting peptide functioning as both a glucagon-like peptide-1 receptor agonist and a glucagon receptor antagonist," *J. Biol. Chem.* 281:12506-12515, 2006.
Parlevliet et al., "Oxyntomodulin ameliorates glucose intolerance in mice fed a high-fat diet," *Am. J. Physiol. Endocrinol. Metab.* 294:E142-E147, 2008.
Pratesi et al., "Poly-L-aspartic acid as a carrier for doxorubicin: a comparative in vivo study of free and polymer-bound drug," *Br. J. Cancer* 52:841-848, 1985.
Tsukada et al., "An anti-α-fetoprotein antibody-daunorubicin conjugate with a novel poly-L-glutamic acid derivative as intermediate drug carrier," *J. Natl. Cancer Inst.* 73:721-729, 1984.
Unson et al., "Glucagon antagonists: contribution to binding and activity of the amino-terminal sequence 1-5, position 12, and the putative α-helical segment 19-27," *J. Biol. Chem.* 264(2):789-794, 1989.
Unson et al., "Identification of an essential serine residue in glucagon: implication for an active site triad," *Proc. Natl. Acad. Sci. U.S.A.* 91:454-458, 1994.
Unson et al., "Positively charged residues at positions 12, 17, and 18 of glucagon ensure maximum biological potency," *J. Biol. Chem.* 273:10308-10312, 1998.
Zalipsky, "Functionalized poly(ethylene glycol) for preparation of biologically relevant conjugates," *Bioconjugate Chem.* 6:150-165, 1995.
Zhu et al.,"The Role of Dipeptidyl Peptidase IV in the Cleavage of Glucagon Family Peptides: In Vivo Metabolism of Pituitary Adenylate Cyclase Activating Polypeptide-(1-38)," *J. Biol. Chem.* 278:22418-22423, 2003.
U.S. Appl. No. 14/516,216, Riber et al.
U.S. Appl. No. 14/517,497, Riber et al.
U.S. Appl. No. 14/195,533, Meier et al.
Jaya et al., "Mechanism of hypocholesterolemic action of glucagon." J Biosci. 12(2):111-4 (1987).
Hostrup et al., Modification of Peptides and Proteins. *Delivery Technologies for Biopharmaceuticals: Peptides, Proteins, Nucleic Acids and Vaccines*. Wiley & Sons, 171-91 (2009).
Parlevliet et al., "CNTO736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Wermuth, "Glossary of terms used in medicinal chemistry," Pure & Appl Chem. 70(5):1129-43 (1998).
Written Opinion for Singapore Application No. 201209089-0 dated Nov. 8, 2013 (10 pages).
International Search Report for International Application No. PCT/IB2012/000134, mailed Jun. 25, 2012 (3 pages).

(56) References Cited

OTHER PUBLICATIONS

Communucation from the European Patent Office for European Patent Application No. 08 875 673.9-2405 dated Jul. 4, 2012 (6 pages).
European Search Report from European Patent Application No. 07016032.0, completed Jan. 28, 2008 (8 pages).
International Preliminary Report on Patentability for PCT/GB2008/002041, issued Dec. 17, 2009 (7 pages).
International Search Report and Written Opinion for PCT/GB2008/004132 mailed Jun. 10, 2009 (9 pages).
Protest of U.S. Appl. No. 12/664,534 Pursuant 37 CFR 1.291, mailed Jan. 13, 2010 (14 pages).
International Search Report for PCT/GB2008/002041, completed Aug. 28, 2008, mailed Sep. 9, 2008 (3 pages).
International Search Report for PCT/GB2008/004157, mailed Jun. 4, 2009 (21 pages).
International Search Report and Written Opinion for PCT/GB2008/004121, mailed Jun. 30, 2009 (25 pages).
International Search Report and Written Opinion for PCT/GB2008/004130, mailed Mar. 25, 2009 (17 pages).
International Search Report for PCT/DK2010/000099, mailed Dec. 2, 2010 (2 pages).
International Search Report for PCT/DK2011/000067, mailed Dec. 9, 2011 (4 pages).
Pocai, "Glucagon signaling in the heart: activation or inhibition?," Mol Metab. 4(2):81-2 (2015).
Goldstein et al., "Effects of chronic heart failure on the capacity of glucagon to enhance contractility and adenyl cyclase activity of human papillary muscles," Circulation. 44(4):638-648 (1971).
Arnold, "Heart failure," <http://www.merckmanuals.com/home/heart_and_blood_vessel_disorders/heart_failure/heart_fail ure.html?qt=congestive heart failure&alt=sh>, retrieved on Feb. 8, 2015 (12 pages).
Mehta, "Diabetic cardiomyopathy: insights into pathogenesis, diagnostic challenges, and therapeutic options," Intl J Pharm Sci Res. 3(10):3565-3576 (2012).
Ali et al., "Cardiomyocyte glucagon receptor signaling modulates outcomes in mice with experimental myocardial infarction," Mol Metab. 4(2):132-143 (2015).
Pocai et al., "Glucagon-like peptide 1/glucagon receptor dual agonism reverses obesity in mice," Diabetes. 58(10):2258-66 (2009).
Rose et al., "Insulin proteinase liberates from glucagon a fragment known to have enhanced activity against $Ca^{2+} + Mg^{2+}$ -dependent ATPase," Biochem J. 256(3):847-51 (1988).
International Preliminary Report on Patentability for PCT/EP2013/069286, completed Jan. 19, 2015 (40 pages).
International Search Report and Written Opinion for PCT/EP2013/069286, mailed Dec. 18, 2013 (16 pages).
Written Opinion for PCT/DK2011/000072, mailed Dec. 6, 2011 (6 pages).

GLUCAGON ANALOGUES

CROSS-REFERENCE TO RELATED APPLICATIONS

This application claims priority under 35 U.S.C. §371 from International Application No. PCT/DK2011/000072, filed on Jun. 24, 2011, which claims benefit of Danish Application No. PA 2010 00558, filed on Jun. 24, 2010 and U.S. Provisional Application No. 61/358,614, filed on Jun. 25, 2010.

FIELD OF THE INVENTION

The present invention relates to glucagon analogues and their medical use, for example in the treatment of obesity and diabetes.

BACKGROUND OF THE INVENTION

Obesity and diabetes are globally increasing health problems and are associated with various diseases, particularly cardiovascular disease (CVD), obstructive sleep apnea, stroke, peripheral artery disease, microvascular complications and osteoarthritis.

About 250 million people worldwide suffer from diabetes, and by 2025 it is estimated that 380 million will have diabetes. Many have additional cardiovascular risk factors, including high/aberrant LDL and triglycerides and low HDL.

Cardiovascular disease accounts for about 50% of mortality in people with diabetes, and the morbidity and mortality rates relating to obesity and diabetes underscore the medical need for efficacious treatment options.

Preproglucagon is a 158 amino acid precursor polypeptide that is differentially processed in the tissues to form a number of structurally related proglucagon-derived peptides, including glucagon (Glu), glucagon-like peptide-1 (GLP-1), glucagon-like peptide-2 (GLP-2) and oxyntomodulin (OXM). These molecules are involved in a wide variety of physiological functions, including glucose homeostasis, insulin secretion, gastric emptying and intestinal growth, as well as regulation of food intake.

Glucagon is a 29-amino acid peptide that corresponds to amino acids 53 to 81 of pre-proglucagon, and has the following amino acid sequence (written using conventional three-letter amino acid abbreviations): His Ser-Gln-Gly-Thr-Phe-Thr-Ser-Lys-Tyr-Leu-Asp-Ser-Arg-Arg-Ala-Gln-Asp-Phe-Val-Gln-Trp-Lue-Met-Asn-Thr (SEQ ID NO:86). The amino acid sequence of glucagon written using conventional one-letter amino acid abbreviations is: HSQGTFTSDYSKYLD-SRRAQDFVQWLMNT (SEQ ID NO:86).

Oxyntomodulin (OXM) is a 37-amino acid peptide which includes the complete 29-amino acid sequence of glucagon with an octapeptide carboxy-terminal extension. The latter extension consists of amino acids 82 to 89 of pre-proglucagon, having the sequence Lys-Arg-Asn-Arg-Asn-Asn-Ile-Ala and termed "intervening peptide 1" or IP-1; the full sequence of human oxyntomodulin is thus His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg- Asn-Asn-Ile-Ala (SEQ ID NO:87).

The major biologically active fragment of GLP-1 is produced as a 30-amino acid, C-terminally amidated peptide that corresponds to amino acids 98 to 127 of pre-proglucagon.

Glucagon helps maintain the level of glucose in the blood by binding to glucagon receptors on hepatocytes, causing the liver to release glucose—stored in the form of glycogen—through glycogenolysis. As these stores become depleted, glucagon stimulates the liver to synthesize additional glucose by gluconeogenesis. This glucose is released into the bloodstream, preventing the development of hypoglycemia. Additionally, glucagon has been demonstrated to increase lipolysis and decrease body weight.

GLP-1 decreases elevated blood glucose levels by improving glucose-stimulated insulin secretion. It also promotes weight loss, primarily through decreasing food intake.

Oxyntomodulin is released into the blood in response to food ingestion and in proportion to meal calorie content. The mechanism of action of oxyntomodulin is not well understood. In particular, it is not known whether the effects of the hormone are mediated exclusively through the glucagon receptor and the GLP-1 receptor, or through one or more as-yet unidentified receptors.

Other peptides have been shown to bind and activate both the glucagon and the GLP-1 receptor (see, e.g., Hjort et al, Journal of Biological Chemistry, 269, 30121-30124, 1994) and to suppress body weight gain and reduce food intake (WO 2006/134340; WO 2007/100535; WO 2008/101017).

Among the amino acid residues in the sequence of native glucagon, the residues and positions 3 and 4 (Gln and Gly, respectively, in native human glucagon), respectively, appear to be rather generally regarded as not being susceptible to substitution without loss of physiological activity. However, the present inventors believe that the observed, relatively facile deamidation of the Gln residue at position 3 of native glucagon is to a large extent associated with the presence of the sterically small Gly residue in the neighbouring 4 position. It would thus be highly desirable to be able to substitute, inter alia, one or both of the residues at positions 3 and 4 and still be able to achieve peptides possessing useful physiological activity.

SUMMARY OF THE INVENTION

The present invention thus relates, inter alia, to glucagon analogues that comprise substitutions of the amino acid residues at positions 3 and/or 4 of native glucagon, and which generally exhibit useful physiological activity, such as significant activity at the glucagon receptor and/or the GLP-1 receptor.

The invention provides a compound having the formula:

wherein
$R^1$ is H, $C_{1-4}$ alkyl, acetyl, formyl, benzoyl or trifluoroacetyl (such as H or acetyl, often suitably H);
$R^2$ is OH or $NH_2$ (often suitably $NH_2$); and
Z is a peptide having the formula I:

```
                                              (SEQ ID NO: 85)
His-X2-X3-X4-Thr-Phe-Thr-Ser-Asp-Tyr-Ser-Lys-Tyr-

Leu-X15-Ser-X17-Ala-Ala-X20-X21-Phe-Val-X24-Trp-

Leu-X27-X28-Ala  (I);
``` wherein
X2 is Aib, Ser or Gly;
X3 is Gln, Glu, Gly, His, Phe, Leu, Trp, Tyr, Val, Arg, Ala, Ser, Ile, Pro, Hph, Hse, Cit, 1-Nal or 3-(heterocyclyl)alanine;
X4 is Gly, Ala, D-Ala, Val, Aib, Leu, D-Leu, Pro, Glu, Phe, D-Phe, Arg or Lys;
X15 is Asp or Glu;
X17 is Arg or X;
X20 is Arg, His or X;
X21 is Asp or Glu;

X24 is Ala or X;
X27 is Leu or X;
X28 is Arg or X;
wherein each residue X is independently selected from the group consisting of Glu, Lys, Ser, Cys, Dbu, Dpr and Orn; and wherein the side-chain of at least one amino acid residue X is optionally conjugated to a lipophilic substituent having the formula:
(i) $Z^1$, wherein $Z^1$ is a lipophilic moiety conjugated directly to the side chain of X; or
(ii) $Z^1Z^2$, wherein $Z^1$ is a lipophilic moiety, $Z^2$ is a spacer, and $Z^1$ is conjugated to the side chain of X via $Z^2$;
with the proviso that if X3 is Gln, then X4 is not Gly.

Pharmaceutically acceptable salts or solvates, e.g. hydrates, of compounds of the invention are also within the scope of the invention.

A further aspect of the present invention relates to a composition comprising a compound of the invention as defined herein, or a salt or derivative (e.g. solvate) thereof, together with a carrier. In preferred embodiments, the composition is a pharmaceutically acceptable composition and the carrier is a pharmaceutically acceptable carrier. Where relevant, the salt in question may be a pharmaceutically acceptable acid addition salt of the compound, e.g. an acetate, trifluoroacetate or chloride salt.

Compounds of the invention as disclosed herein may be useful in preventing weight gain or promoting weight loss. By "preventing" is meant inhibiting or reducing weight gain when compared to the absence of treatment, and is not necessarily meant to imply complete cessation of weight gain. Compounds of the invention may achieve an observed effect on body weight by causing a decrease in food intake and/or increase in energy expenditure. Independently of their effect on body weight, the compounds of the invention may have a beneficial effect on circulating glucose levels and/or on glucose tolerance. They may also, or alternatively, have a beneficial effect on circulating cholesterol levels as a result of lowering circulating LDL levels and increasing HDL/LDL ratio. Thus, compounds of the invention may be used for direct or indirect therapy of a condition caused or characterised by excess body weight, such as the treatment and/or prevention of obesity, morbid obesity, obesity linked inflammation, obesity-linked gallbladder disease or obesity-induced sleep apnea. They may also be used for the treatment of pre-diabetes, insulin resistance, glucose intolerance, type 2 diabetes, type I diabetes, hypertension or atherogenic dyslipidaemia (or a combination of two or more of these metabolic risk factors), atherosclerois, arteriosclerosis, coronary heart disease, peripheral artery disease, stroke and/or microvascular disease. Their effect on these conditions may be as a result of, or associated with, their effect on body weight, or may be independent thereof.

Thus, another aspect of the invention relates to the use of a compound of the invention in the treatment of a condition as described above, in an individual in need thereof.

A still further aspect of the invention relates to a compound of the invention for use in a method of medical treatment, particularly for use in a method of treatment of a condition as described above.

Yet another aspect of the invention relates to the use of a compound of the invention in the preparation of a medicament for the treatment of a condition as described above.

DETAILED DESCRIPTION OF THE INVENTION

Throughout this specification, the conventional one-letter and three-letter codes for naturally occurring amino acids are used. Where relevant, and unless otherwise indicated, three-letter codes refer to the L-isomeric forms of the amino acids in question. Where appropriate, D-isomeric forms of amino acids are indicated in the conventional manner by the prefix "D" before the conventional three-letter code (e.g. DPhe, DLeu, etc.). Generally accepted three-letter codes are employed for a number of non-naturally occurring amino acids, including Aib (α-aminoisobutyric acid), Dbu (2,4-diaminobutyric acid), Dpr (2,3-diaminopropionic acid), Cit (citrulline), 1Nal (1-naphthylalanine), Hph (homophenylalanine), Hse (homoserine) and Orn (ornithine).

The term "native glucagon" refers to native human glucagon having the sequence H-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH (SEQ ID NO:86).

As already indicated above, the present invention provides a compound having the formula:

$R^1$—Z—$R^2$ wherein
$R^1$ is H, $C_{1-4}$ alkyl, acetyl, formyl, benzoyl or trifluoroacetyl (such as H or acetyl, often suitably H);
$R^2$ is OH or $NH_2$ (often suitably $NH_2$); and
Z is a peptide having the formula I:

(SEQ ID NO: 85)
His-X2-X3-X4-Thr-Phe-Thr-Ser-Asp-Tyr-Ser-Lys-Tyr-

Leu-X15-Ser-X17-Ala-Ala-X20-X21-Phe-Val-X24-Trp-

Leu-X27-X28-Ala 

wherein
X2 is Aib, Ser or Gly;
X3 is Gln, Glu, Gly, His, Phe, Leu, Trp, Tyr, Val, Arg, Ala, Ser, Ile, Pro, Hph, Hse, Cit, 1-Nal or 3-(heterocyclyl)alanine;
X4 is Gly, Ala, D-Ala, Val, Aib, Leu, D-Leu, Pro, Glu, Phe, D-Phe, Arg or Lys;
X15 is Asp or Glu;
X17 is Arg or X;
X20 is Arg, His or X;
X21 is Asp or Glu;
X24 is Ala or X;
X27 is Leu or X;
X28 is Arg or X;
wherein each residue X is independently selected from the group consisting of Glu, Lys, Ser, Cys, Dbu, Dpr and Orn; and wherein the side-chain of at least one amino acid residue X is optionally conjugated to a lipophilic substituent having the formula:
(i) $Z^1$, wherein $Z^1$ is a lipophilic moiety conjugated directly to the side chain of X; or
(ii) $Z^1Z^2$, wherein $Z^1$ is a lipophilic moiety, $Z^2$ is a spacer, and $Z^1$ is conjugated to the side chain of X via $Z^2$;
with the proviso that if X3 is Gln, then X4 is not Gly.

In certain embodiments of compounds of the invention wherein the amino acid residue X3 is 3-(heterocyclyl)alanyl [i.e. an amino acid residue deriving from a 3-(heterocyclyl)-substituted alanine], then X3 may suitably be selected from the group consisting of 3-(2-furyl)alanyl, 3-(4-thiazolyl)alanyl, 3-(3-pyridyl)alanyl, 3-(4-pyridyl)alanyl, 3-(1-pyrazolyl)alanyl, 3-(2-thienyl)alanyl, 3-(3-thienyl)alanyl and 3-(1,2,4-triazol-1-yl)alanyl.

In certain embodiments of compounds of the invention, such as embodiments exhibiting significant agonist activity towards both the GLP-1 receptor and the glucagon receptor (vide infra) a, X3 may advantageously be selected among Gln, His, Ile, Tyr, Pro, Hse, 3-(4-thiazolyl)alanyl, 3-(3-pyridyl)alanyl, 3-(2-thienyl)alanyl, 3-(3-thienyl)alanyl and 3-(1,2,4-triazol-1-yl)alanyl. In such embodiments X4 may further advantageously be selected among Gly, D-Ala, D-Leu and D-Phe.

In certain other embodiments of compounds of the invention, such as embodiments primarily exhibiting significant agonist activity towards the GLP-1 receptor, but lesser activity towards the glucagon receptor (vide infra), X3 may advantageously be selected among Glu, Gly, Leu, Val, Ala, Ser, Cit, 3-(2-furyl)alanyl and 3-(1-pyrazolyl)alanyl. In such embodiments X4 may further advantageously be Gly.

The amino acid sequence of a compound of the invention differs from that of native glucagon at least at one of positions 3 and 4, and in all cases at positions 18, 20, 24, 27, 28 and 29. In addition, it may differ from that of native glucagon at both of positions 3 and 4, and at one or more of positions 2, 17 and 21.

In certain embodiments of compounds of the invention, any residue X, and especially a residue X which is conjugated to a lipophilic substituent, is independently selected from Lys, Glu, Dbu, Dpr and Orn.

In certain embodiments,
X17 is selected from Lys and Cys;
X20 is selected from His, Lys, Arg and Cys;
X24 is selected from Lys, Glu and Ala;
X27 is selected from Leu and Lys; and/or
X28 is selected from Ser, Arg and Lys.

Specific combinations of amino acid residues which may be present in the peptide of formula I include the following:
X2 is Aib and X17 is Lys;
X2 is Aib and X17 is Cys;
X2 is Aib and X20 is Cys;
X2 is Aib and X28 is Lys;
X17 is Lys and X20 is Lys;
X17 is Lys and X21 is Asp;
X17 is Lys and X24 is Glu;
X17 is Lys and X27 is Leu;
X17 is Lys and X27 is Lys;
X17 is Lys and X28 is Ser;
X17 is Lys and X28 is Arg;
X20 is Lys and X27 is Leu;
X21 is Asp and X27 is Leu;
X17 is Lys, X24 is Glu and X28 is Arg;
X17 is Lys, X24 is Glu and X28 is Lys;
X17 is Lys, X27 is Leu and X28 is Ser;
X17 is Lys, X27 is Leu and X28 is Arg;
X20 is Lys, X24 is Glu and X27 is Leu;
X20 is Lys, X27 is Leu and X28 is Ser;
X20 is Lys, X27 is Leu and X28 is Arg;
X17 is Lys, X20 is His, X24 is Glu and X28 is Ser;
X17 is Lys, X20 is Lys, X24 is Glu and X27 is Leu; or
X17 is Cys, X20 is Lys, X24 is Glu and X27 is Leu.

It may be desirable that the peptide of formula I contains only one amino acid of the type which is to be derivatised by conjugation to a lipophilic moiety or substituent. For example, the peptide may contain only one Lys residue, only one Cys residue or only one Glu residue to which the lipophilic substituent is to be conjugated.

Compounds of the invention may carry one or more intramolecular bridges within the peptide sequence of formula I. Such a bridge may be formed between the side-chains of two amino acid residues of the peptide sequence of formula I which are typically separated by three amino acid residues in the linear amino acid sequence (i.e. between amino acid residues at respective positions A and A+4).

Such a bridge may be formed between the side-chains of amino acid residues in pairs of amino acid residues at positions 17 and 21, 20 and 24, or 24 and 28, respectively. The two side-chains may be linked to one another through ionic interactions, or by covalent bonds. Thus, for example, such pairs of residues may comprise oppositely charged side-chains in order to form a salt bridge by ionic interaction. For example, one of the residues may be Glu or Asp, while the other may be Lys or Arg. Pairing of Lys and Glu, and of Lys and Asp, may also lead to intermolecular reaction to form a lactam ring.

Examples of relevant pairs of residues at positions 17 and 21 include:
X17 is Arg and X21 is Glu;
X17 is Lys and X21 is Glu;
X17 is Arg and X21 is Asp; and
X17 is Lys and X21 is Asp.

Examples of relevant pairs of residues at positions 20 and 24 include:
X20 is Glu and X24 is Lys;
X20 is Lys and X24 is Glu; and
X20 is Arg and X24 is Glu.

Examples of relevant pairs of residues at positions 24 and 28 include:
X24 is Glu and X28 is Lys;
X24 is Glu and X28 is Arg; and
X24 is Lys and X28 is Glu.

The pairing of Lys and Glu, e.g. to form a lactam ring, may be particularly desirable, especially between positions 24 and 28.

It will be apparent that a residue involved in an intramolecular bridge cannot also be derivatised with a lipophilic substituent.

Without wishing to be bound by any particular theory, it is believed that such intramolecular bridges stabilise the alpha helical structure of the molecule and so increase potency and/or selectivity at the GLP-1 receptor and possibly also at the glucagon receptor.

In certain embodiments of compounds of the invention, the peptide of formula I (i.e. Z) may have an amino acid sequence selected from the following:

```
                                           SEQ ID NO 1
H-Aib-EGTFTSDYSKYLDSKAAHDFVEWLLSA;

SEQ ID NO 2
H-Aib-HGTFTSDYSKYLDSKAAHDFVEWLLSA;

SEQ ID NO 3
H-Aib-QATFTSDYSKYLDSKAAHDFVEWLLSA;

SEQ ID NO 4
H-Aib-QVTFTSDYSKYLDSKAAHDFVEWLLSA;

SEQ ID NO 5
HGQ-Aib-TFTSDYSKYLDSKAAHDFVEWLLSA;

SEQ ID NO 6
HGEGTFTSDYSKYLDSKAAHDFVEWLLSA;

SEQ ID NO 7
HSQ-Aib-TFTSDYSKYLDSKAAHDFVEWLLSA;

SEQ ID NO 8
H-Aib-QLTFTSDYSKYLDSKAAHDFVEWLLSA;

SEQ ID NO 9
H-Aib-QPTFTSDYSKYLDSKAAHDFVEWLLSA;

SEQ ID NO 10
H-Aib-QETFTSDYSKYLDSKAAHDFVEWLLSA;
```

-continued

```
                                              SEQ ID NO 11
H-Aib-Q-Aib-TFTSDYSKYLDSKAAHDFVEWLLSA;

SEQ ID NO 12
H-Aib-QFTFTSDYSKYLDSKAAHDFVEWLLSA;

SEQ ID NO 13
H-Aib-FGTFTSDYSKYLDSKAAHDFVEWLLSA;

SEQ ID NO 14
H-Aib-Q-DPhe-TFTSDYSKYLDSKAAHDFVEWLLSA;

SEQ ID NO 15
H-Aib-QRTFTSDYSKYLDSKAAHDFVEWLLSA;

SEQ ID NO 16
H-Aib-LGTFTSDYSKYLDSKAAHDFVEWLLSA;

SEQ ID NO 17
H-Aib-Hph-GTFTSDYSKYLDSKAAHDFVEWLLSA;

SEQ ID NO 18
H-Aib-WGTFTSDYSKYLDSKAAHDFVEWLLSA;

SEQ ID NO 19
H-Aib-YGTFTSDYSKYLDSKAAHDFVEWLLSA;

SEQ ID NO 20
H-Aib-VGTFTSDYSKYLDSKAAHDFVEWLLSA;

SEQ ID NO 21
H-Aib-QKTFTSDYSKYLDSKAAHDFVEWLLSA;

SEQ ID NO 22
H-Aib-RGTFTSDYSKYLDSKAAHDFVEWLLSA;

SEQ ID NO 23
H-Aib-AGTFTSDYSKYLDSKAAHDFVEWLLSA;

SEQ ID NO 24
H-Aib-SGTFTSDYSKYLDSKAAHDFVEWLLSA;

SEQ ID NO 25
H-Aib-IGTFTSDYSKYLDSKAAHDFVEWLLSA;

SEQ ID NO 26
H-Aib-GGTFTSDYSKYLDSKAAHDFVEWLLSA;

SEQ ID NO 27
H-Aib-PGTFTSDYSKYLDSKAAHDFVEWLLSA;

SEQ ID NO 28
H-Aib-HGTFTSDYSKYLDSKAAHEFVEWLLEA;

SEQ ID NO 29
H-Aib-Cit-GTFTSDYSKYLDSKAAHDFVEWLLSA;

SEQ ID NO 30
H-Aib-Q-DAla-TFTSDYSKYLDSKAAHDFVEWLLSA;

SEQ ID NO 31
H-Aib-Hse-GTFTSDYSKYLDSKAAHDFVEWLLSA;

SEQ ID NO 32
H-Aib-Q-DLeu-TFTSDYSKYLDSKAAHDFVEWLLSA;

SEQ ID NO 33
H-Aib-HGTFTSDYSKYLESKAAEEFVEWLLEA;

SEQ ID NO 34
H-Aib-1Nal-GTFTSDYSKYLDSKAAHDFVEWLLSA;

SEQ ID NO 35
H-Aib-[3-(2-furyl)alanyl]-GTFTSDYSKYLDSKAAHDFVEW
LLSA;

SEQ ID NO 36
H-Aib-[3-(4-thiazolyl)alanyl]-GTFTSDYSKYLDSKAAHD
FVEWLLSA;

SEQ ID NO 37
H-Aib-[3-(3-pyridyl)alanyl]-GTFTSDYSKYLDSKAAHDFV
EWLLSA;

SEQ ID NO 38
H-Aib-[3-(4-pyridyl)alanyl]-GTFTSDYSKYLDSKAAHDFV
EWLLSA;

SEQ ID NO 39
H-Aib-[3-(2-thienyl)alanyl]-GTFTSDYSKYLDSKAAHDFV
EWLLSA;

SEQ ID NO 40
H-Aib-[3-(3-thienyl)alanyl]-GTFTSDYSKYLDSKAAHDFV
EWLLSA;

SEQ ID NO 41
H-Aib-[3-(1-pyrazolyl)alanyl]-GTFTSDYSKYLDSKAAHD
FVEWLLSA;
and

SEQ ID NO 42
H-Aib-[3-(1,2,4-triazol-1-yl)alanyl]-GTFTSDYSKYL
DSKAAHDFVEWLLSA.
```

Each of the latter embodiments, independently, constitutes an individual embodiment of a peptide group Z which may be present in a compound of the invention.

Among preferred embodiments of compounds of the invention are compounds wherein the peptide of formula I (i.e. Z) has an amino acid sequence selected from the following:

```
H-Aib-HGTFTSDYSKYLDSKAAHDFVEWLLSA  (SEQ ID NO: 2);

HGEGTFTSDYSKYLDSKAAHDFVEWLLSA  (SEQ ID NO: 6);

H-Aib-QLTFTSDYSKYLDSKAAHDFVEWLLSA  (SEQ ID NO: 8);

H-Aib-FGTFTSDYSKYLDSKAAHDFVEWLLSA  (SEQ ID NO: 12);

H-Aib-Q-DPhe-TFTSDYSKYLDSKAAHDFVEWLLSA  (SEQ ID NO: 14);

H-Aib-LGTFTSDYSKYLDSKAAHDFVEWLLSA  (SEQ ID NO: 16);

H-Aib-YGTFTSDYSKYLDSKAAHDFVEWLLSA  (SEQ ID NO: 19);

H-Aib-VGTFTSDYSKYLDSKAAHDFVEWLLSA  (SEQ ID NO: 20);

H-Aib-AGTFTSDYSKYLDSKAAHDFVEWLLSA  (SEQ ID NO: 23);

H-Aib-SGTFTSDYSKYLDSKAAHDFVEWLLSA  (SEQ ID NO: 24);

H-Aib-IGTFTSDYSKYLDSKAAHDFVEWLLSA  (SEQ ID NO: 25);
```

```
H-Aib-GGTFTSDYSKYLDSKAAHDFVEWLLSA  (SEQ ID NO: 26);

H-Aib-PGTFTSDYSKYLDSKAAHDFVEWLLSA  (SEQ ID NO: 27);

H-Aib-HGTFTSDYSKYLDSKAAHEFVEWLLEA  (SEQ ID NO: 28);

H-Aib-Cit-GTFTSDYSKYLDSKAAHDFVEWLLSA  (SEQ ID NO: 29);

H-Aib-Q-DAla-TFTSDYSKYLDSKAAHDFVEWLLSA  (SEQ ID NO: 30);

H-Aib-Hse-GTFTSDYSKYLDSKAAHDFVEWLLSA  (SEQ ID NO: 31);

H-Aib-Q-DLeu-TFTSDYSKYLDSKAAHDFVEWLLSA  (SEQ ID NO: 32);

H-Aib-HGTFTSDYSKYLESKAAEEFVEWLLEA  (SEQ ID NO: 33);

H-Aib-[3-(2-furyl)alanyl]-GTFTSDYSKYLDSKAAHDFVEWLLSA  (SEQ ID NO: 35);

H-Aib-[3-(4-thiazolyl)alanyl]-GTFTSDYSKYLDSKAAHDFVEWLLSA  (SEQ ID NO: 36);

H-Aib-[3-(3-pyridyl)alanyl]-GTFTSDYSKYLDSKAAHDFVEWLLSA  (SEQ ID NO: 37);

H-Aib-[3-(2-thienyl)alanyl]-GTFTSDYSKYLDSKAAHDFVEWLLSA  (SEQ ID NO: 39);

H-Aib-[3-(3-thienyl)alanyl]-GTFTSDYSKYLDSKAAHDFVEWLLSA  (SEQ ID NO: 40);

H-Aib-[3-(1-pyrazoly)alanyl]-GTFTSDYSKYLDSKAAHDFVEWLLSA  (SEQ ID NO: 41);
and

H-Aib-[3-(1,2,4-triazol-1-yl)alanyl]-GTFTSDYSKYLDSKAAHDFVEWLLSA  (SEQ ID NO:
 42).
```

As before, each of the latter embodiments, independently, constitutes an individual embodiment of a peptide group Z which may be present in a compound of the invention.

In certain embodiments of these latter peptides of formula I, the lysine (K) residue at position 17 may carry (i.e. be conjugated to) a lipophilic substituent, as elucidated further below.

More generally, the side-chain(s) of one or more of the residues X (vide supra) in a compound of the invention may be conjugated to a lipophilic substituent. For example, a side-chain of one residue X may be conjugated to a lipophilic substituent. Alternatively, the side-chains of two, or even more than two, residues X may be conjugated to a lipophilic substituent; by way of example, at least one of X17, X20 and X28 may be conjugated to a lipophilic substituent.

Thus, a compound of the invention may have just one amino acid residue that is conjugated to a lipophilic substituent, at position 17, 20, 24, 27 or 28, such as at position 17 or 20, and often preferably at position 17.

Alternatively, the compound may comprise precisely two lipophilic substituents, each conjugated to a respective amino acid residue at one of positions 17, 20, 24, 27 or 28. Preferably, one or both of the latter lipophilic substituents are present on a respective amino acid residue at one of positions 17 or 20. Thus, the compound may have two lipophilic substituents on respective amino acid residues at positions 17 and 20, 17 and 24, 17 and 27, or 17 and 28; at 20 and 24, 20 and 27, or 20 and 28; at 24 and 27, or 24 and 28; or at 27 and 28.

In yet further embodiments of a compound of the invention, the compound may have one or more further lipophilic substituents (giving three or more in total), each conjugated to a respective amino acid residue at further positions selected from positions 17, 20, 24, 27 or 28. However, it may be desirable that a maximum of two amino acid positions are derivatized in this way.

The lipophilic moiety $Z^1$ may comprise a hydrocarbon chain having from 10 to 24 C atoms, e.g. from 10 to 22 C atoms, such as from 10 to 20 C atoms. It may have at least 11 C atoms, and/or at most 18 C atoms. For example, the hydrocarbon chain may contain 12, 13, 14, 15, 16, 17 or 18 carbon atoms. Thus, for example, $Z^1$ may be a dodecanoyl, 2-butyloctanoyl, tetradecanoyl, pentadecanoyl, hexadecanoyl, heptadecanoyl, octadecanoyl or eicosanoyl moiety.

Independently, where present, $Z^2$ may be or comprise one or more amino acid residues. For example, $Z^2$ may be a γ-Glu (also denoted isoGlu), Glu, β-Ala or ε-Lys residue, or a 4-aminobutanoyl, 8-aminooctanoyl or 8-amino-3,6-dioxaoctanoyl moiety.

Suitable $Z^1Z^2$ moieties include, but are not limited to, dodecanoyl-γ-Glu, hexadecanoyl-γ-Glu (also denoted hexadecanoyl-isoGlu), hexadecanoyl-Glu, hexadecanoyl-[3-aminopropanoyl], hexadecanoyl-[8-aminooctanoyl], hexadecanoyl-ε-Lys, 2-butyloctanoyl-γ-Glu, octadecanoyl-γ-Glu and hexadecanoyl-[4-aminobutanoyl].

In certain embodiments, Z may have the formula:

```
                                                              SEQ ID NO 43
H-Aib-EGTFTSDYSKYLDSK(hexadecanoyl-isoGlu)-AAHDFVEWLLSA SEQ ID NO 44
H-Aib-HGTFTSDYSKYLDSK(hexadecanoyl-isoGlu)-AAHDFVEWLLSA;

SEQ ID NO 45
H-Aib-QATFTSDYSKYLDSK(hexadecanoyl-isoGlu)-AAHDFVEWLLSA;

SEQ ID NO 46
H-Aib-QVTFTSDYSKYLDSK(hexadecanoyl-isoGlu)-AAHDFVEWLLSA;
```

-continued

| | |
|---|---|
| HGQ-Aib-TFTSDYSKYLDSK(hexadecanoyl-isoGlu)-AAHDFVEWLLSA; | SEQ ID NO 47 |
| HGEGTFTSDYSKYLDSK(hexadecanoyl-isoGlu)-AAHDFVEWLLSA; | SEQ ID NO 48 |
| HSQ-Aib-TFTSDYSKYLDSK(hexadecanoyl-isoGlu)-AAHDFVEWLLSA; | SEQ ID NO 49 |
| H-Aib-QLTFTSDYSKYLDSK(hexadecanoyl-isoGlu)-AAHDFVEWLLSA; | SEQ ID NO 50 |
| H-Aib-QPTFTSDYSKYLDSK(hexadecanoyl-isoGlu)-AAHDFVEWLLSA; | SEQ ID NO 51 |
| H-Aib-QETFTSDYSKYLDSK(hexadecanoyl-isoGlu)-AAHDFVEWLLSA; | SEQ ID NO 52 |
| H-Aib-Q-Aib-TFTSDYSKYLDSK(hexadecanoyl-isoGlu)-AAHDFVEWLLSA; | SEQ ID NO 53 |
| H-Aib-QFTFTSDYSKYLDSK(hexadecanoyl-isoGlu)-AAHDFVEWLLSA; | SEQ ID NO 54 |
| H-Aib-FGTFTSDYSKYLDSK(hexadecanoyl-isoGlu)-AAHDFVEWLLSA; | SEQ ID NO 55 |
| H-Aib-Q-DPhe-TFTSDYSKYLDSK(hexadecanoyl-isoGlu)-AAHDFVEWLLSA; | SEQ ID NO 56 |
| H-Aib-QRTFTSDYSKYLDSK(hexadecanoyl-isoGlu)-AAHDFVEWLLSA; | SEQ ID NO 57 |
| H-Aib-LGTFTSDYSKYLDSK(hexadecanoyl-isoGlu)-AAHDFVEWLLSA; | SEQ ID NO 58 |
| H-Aib-Hph-GTFTSDYSKYLDSK(hexadecanoyl-isoGlu)-AAHDFVEWLLSA; | SEQ ID NO 59 |
| H-Aib-WGTFTSDYSKYLDSK(hexadecanoyl-isoGlu)-AAHDFVEWLLSA; | SEQ ID NO 60 |
| H-Aib-YGTFTSDYSKYLDSK(hexadecanoyl-isoGlu)-AAHDFVEWLLSA; | SEQ ID NO 61 |
| H-Aib-VGTFTSDYSKYLDSK(hexadecanoyl-isoGlu)-AAHDFVEWLLSA; | SEQ ID NO 62 |
| H-Aib-QKTFTSDYSKYLDSK(hexadecanoyl-isoGlu)-AAHDFVEWLLSA; | SEQ ID NO 63 |
| H-Aib-RGTFTSDYSKYLDSK(hexadecanoyl-isoGlu)-AAHDFVEWLLSA; | SEQ ID NO 64 |
| H-Aib-AGTFTSDYSKYLDSK(hexadecanoyl-isoGlu)-AAHDFVEWLLSA; | SEQ ID NO 65 |
| H-Aib-SGTFTSDYSKYLDSK(hexadecanoyl-isoGlu)-AAHDFVEWLLSA; | SEQ ID NO 66 |
| H-Aib-IGTFTSDYSKYLDSK(hexadecanoyl-isoGlu)-AAHDFVEWLLSA; | SEQ ID NO 67 |
| H-Aib-GGTFTSDYSKYLDSK(hexadecanoyl-isoGlu)-AAHDFVEWLLSA; | SEQ ID NO 68 |
| H-Aib-PGTFTSDYSKYLDSK(hexadecanoyl-isoGlu)-AAHDFVEWLLSA; | SEQ ID NO 69 |
| H-Aib-HGTFTSDYSKYLDSK(hexadecanoyl-isoGlu)-AAHEFVEWLLEA; | SEQ ID NO 70 |
| H-Aib-Cit-GTFTSDYSKYLDSK(hexadecanoyl-isoGlu)-AAHDFVEWLLSA; | SEQ ID NO 71 |
| H-Aib-Q-DAla-TFTSDYSKYLDSK(hexadecanoyl-isoGlu)-AAHDFVEWLLSA; | SEQ ID NO 72 |
| H-Aib-Hse-GTFTSDYSKYLDSK(hexadecanoyl-isoGlu)-AAHDFVEWLLSA; | SEQ ID NO 73 |

H-Aib-Q-DLeu-TFTSDYSKYLDSK(hexadecanoyl-isoGlu)-AAHDFVEWLLSA; (SEQ ID NO 74)

H-Aib-HGTFTSDYSKYLESK(hexadecanoyl-isoGlu)-AAEEFVEWLLEA; (SEQ ID NO 75)

H-Aib-1Nal-GTFTSDYSKYLDSK(hexadecanoyl-isoGlu)-AAHDFVEWLLSA; (SEQ ID NO 76)

H-Aib-[3-(2-furyl)alanyl]-GTFTSDYSKYLDSK(hexadecanoyl-isoGlu)-AAHDFVEWLLSA; (SEQ ID NO 77)

H-Aib-[3-(4-thiazolyl)alanyl]-GTFTSDYSKYLDSK(hexadecanoyl-isoGlu)-AAHDFVEWLLSA; (SEQ ID NO 78)

H-Aib-[3-(3-pyridyl)alanyl]-GTFTSDYSKYLDSK(hexadecanoyl-isoGlu)-AAHDFVEWLLSA; (SEQ ID NO 79)

H-Aib-[3-(4-pyridyl)alanyl]-GTFTSDYSKYLDSK(hexadecanoyl-isoGlu)-AAHDFVEWLLSA; (SEQ ID NO 80)

H-Aib-[3-(2-thienyl)alanyl]-GTFTSDYSKYLDSK(hexadecanoyl-isoGlu)-AAHDFVEWLLSA; (SEQ ID NO 81)

H-Aib-[3-(3-thienyl)alanyl]-GTFTSDYSKYLDSK(hexadecanoyl-isoGlu)-AAHDFVEWLLSA; (SEQ ID NO 82)

H-Aib-[3-(1-pyrazolyl)alanyl]-GTFTSDYSKYLDSK(hexadecanoyl-isoGlu)-AAHDFVEWLLSA; (SEQ ID NO 83)
or H-Aib-[3-(1,2,4-triazol-1-yl)alanyl]-GTFTSDYSKYLDSK(hexadecanoyl-isoGlu)-AAHDFVEWLLSA. (SEQ ID NO 84)

Each of the latter embodiments, independently, constitutes an individual embodiment of a peptide group Z which may be present in a compound of the invention.

Among preferred embodiments of compounds of the invention are compounds wherein the peptide of formula I (i.e. Z) has an amino acid sequence selected from the following:

H-Aib-HGTFTSDYSKYLDSK(hexadecanoyl-isoGlu)-AAHDFVEWLLSA (SEQ ID NO: 44);

HGEGTFTSDYSKYLDSK(hexadecanoyl-isoGlu)-AAHDFVEWLLSA (SEQ ID NO: 48);

H-Aib-QLTFTSDYSKYLDSK(hexadecanoyl-isoGlu)-AAHDFVEWLLSA (SEQ ID NO: 50);

H-Aib-FGTFTSDYSKYLDSK(hexadecanoyl-isoGlu)-AAHDFVEWLLSA (SEQ ID NO: 55);

H-Aib-Q-DPhe-TFTSDYSKYLDSK(hexadecanoyl-isoGlu)-AAHDFVEWLLSA (SEQ ID NO: 56);

H-Aib-LGTFTSDYSKYLDSK(hexadecanoyl-isoGlu)-AAHDFVEWLLSA (SEQ ID NO: 58);

H-Aib-YGTFTSDYSKYLDSK(hexadecanoyl-isoGlu)-AAHDFVEWLLSA (SEQ ID NO: 61);

H-Aib-VGTFTSDYSKYLDSK(hexadecanoyl-isoGlu)-AAHDFVEWLLSA (SEQ ID NO: 62);

H-Aib-AGTFTSDYSKYLDSK(hexadecanoyl-isoGlu)-AAHDFVEWLLSA (SEQ ID NO: 65);

H-Aib-SGTFTSDYSKYLDSK(hexadecanoyl-isoGlu)-AAHDFVEWLLSA (SEQ ID NO: 66);

H-Aib-IGTFTSDYSKYLDSK(hexadecanoyl-isoGlu)-AAHDFVEWLLSA (SEQ ID NO: 67);

H-Aib-GGTFTSDYSKYLDSK(hexadecanoyl-isoGlu)-AAHDFVEWLLSA (SEQ ID NO: 68);

H-Aib-PGTFTSDYSKYLDSK(hexadecanoyl-isoGlu)-AAHDFVEWLLSA (SEQ ID NO: 69);

H-Aib-HGTFTSDYSKYLDSK(hexadecanoyl-isoGlu)-AAHEFVEWLLEA (SEQ ID NO: 70);

H-Aib-Cit-GTFTSDYSKYLDSK(hexadecanoyl-isoGlu)-AAHDFVEWLLSA (SEQ ID NO: 71);

H-Aib-Q-DAla-TFTSDYSKYLDSK(hexadecanoyl-isoGlu)-AAHDFVEWLLSA (SEQ ID NO: 72);

H-Aib-Hse-GTFTSDYSKYLDSK(hexadecanoyl-isoGlu)-AAHDFVEWLLSA (SEQ ID NO: 73);

-continued

```
H-Aib-Q-DLeu-TFTSDYSKYLDSK(hexadecanoyl-isoGlu)-AAHDFVEWLLSA (SEQ ID NO: 74);

H-Aib-HGTFTSDYSKYLESK(hexadecanoyl-isoGlu)-AAEEFVEWLLEA (SEQ ID NO: 75);

H-Aib-[3-(2-furyl)alanyl]-GTFTSDYSKYLDSK(hexadecanoyl-isoGlu)-AAHDFVEWLLSA (SEQ ID NO: 77);

H-Aib-[3-(4-thiazolyl)alanyl]-GTFTSDYSKYLDSK(hexadecanoyl-isoGlu)-AAHDFVEWLLSA (SEQ ID NO: 78);

H-Aib-[3-(3-pyridyl)alanyl]-GTFTSDYSKYLDSK(hexadecanoyl-isoGlu)-AAHDFVEWLLSA (SEQ ID NO: 79);

H-Aib-[3-(2-thienyl)alanyl]-GTFTSDYSKYLDSK(hexadecanoyl-isoGlu)-AAHDFVEWLLSA (SEQ ID NO: 81);

H-Aib-[3-(3-thienyl)alanyl]-GTFTSDYSKYLDSK(hexadecanoyl-isoGlu)-AAHDFVEWLLSA (SEQ ID NO: 82);

H-Aib-[3-(1-pyrazolyl)alanyl]-GTFTSDYSKYLDSK(hexadecanoyl-isoGlu)-AAHDFVEWLLSA (SEQ ID NO: 83);
and H-Aib-[3-(1,2,4-triazol-1-yl)alanyl]-GTFTSDYSKYLDSK(hexadecanoyl-isoGlu)-AAHDFVEWLLSA (SEQ ID NO: 84).
```

As before, each of the latter embodiments, independently, constitutes an individual embodiment of a peptide group Z which may be present in a compound of the invention Native glucagon has Arg at position 18. Compounds of the invention have the small hydrophobic amino acid residue Ala at position 18, which is believed to be capable of increasing potency at both glucagon and GLP-1 receptors, but particularly at the GLP-1 receptor.

The amino acid residues at positions 27, 28 and 29 of native glucagon appear to provide significant selectivity for the glucagon receptor. Substitutions at these positions relative to the native glucagon sequence, particularly the introduction of Ala at position 29, may increase potency at and/or selectivity for the GLP-1 receptor, potentially without significant reduction of potency at the glucagon receptor. Further substitutions which may be incorporated in compounds of the invention include Leu at position 27 and Arg at position 28. Furthermore, Arg at position 28 may be particularly preferred when there is a Glu at position 24 with which it can form an intramolecular bridge, since this may increase its effect on potency at the GLP-1 receptor.

The substitution of the naturally occurring Met residue at position 27 of glucagon (e.g. with Leu, Lys or Glu) also reduces the potential for oxidation, thereby increasing the chemical stability of the compounds.

Substitution of the naturally occurring Asn residue at position 28 of glucagon (e.g. by Arg or Ser) also reduces the potential for deamidation in acidic solution, thereby increasing the chemical stability of the compounds.

Potency and/or selectivity at the GLP-1 receptor, potentially without significant loss of potency at the glucagon receptor, may also be increased by introducing residues that are likely to stabilise an alpha-helical structure in the C-terminal portion of the peptide. It may be desirable, but is not believed essential, for this helical portion of the molecule to have an amphipathic character. Introduction of a residue such as Ala at position 24 may assist. Additionally or alternatively, charged amino acid residues may be introduced at one or more of positions 20, 24, and 28. Thus, the residues at positions 24 and 28 may both be charged, or the residues at positions 20, 24, and 28 may all be charged. For example, the residue at position 20 may be His or Arg, particularly His. The residue at position 24 may be Glu, Lys or Ala, particularly Glu. The residue at position 28 may be Arg. Formation of an intramolecular bridge in this portion of the molecule, e.g. between positions 24 and 28, as discussed above may also contribute to stabilizing the helical character.

Substitution of one or both of the naturally-occurring Gln residues present at positions 20 and 24 of glucagon also reduces the potential for deamidation in acidic solution, so increasing the chemical stability of the compounds.

The side-chain of one or more of the amino acid residues designated X (which may occur at positions 17, 20, 24, 27 and/or 28) may be conjugated to a lipophilic substituent. It will be appreciated that conjugation of the lipophilic substituent to a particular side-chain may affect (e.g. reduce to some extent) certain of the benefits (e.g. with respect to receptor binding) which the unconjugated side chain may provide at that position. However, it is believed that such conjugation with a lipophilic substituent may be beneficial in other ways, e.g. with regard to the physiological stability (half-life) of the compound in question.

Examples of individual compounds of the invention [in all of which the N-terminal group $R^1$ is hydrogen (H) and the C-terminal group $R^2$ is an amino group ($NH_2$)] are the following:

```
H-H-Aib-EGTFTSDYSKYLDSK(hexadecanoyl-isoGlu)-AAHDFVEWLLSA-NH2 (SEQ ID NO: 43);

H-H-Aib-HGTFTSDYSKYLDSK(hexadecanoyl-isoGlu)-AAHDFVEWLLSA-NH2 (SEQ ID NO: 44);

H-H-Aib-QATFTSDYSKYLDSK(hexadecanoyl-isoGlu)-AAHDFVEWLLSA-NH2 (SEQ ID NO: 45);

H-H-Aib-QVTFTSDYSKYLDSK(hexadecanoyl-isoGlu)-AAHDFVEWLLSA-NH2 (SEQ ID NO: 46);

H-HGQ-Aib-TFTSDYSKYLDSK(hexadecanoyl-isoGlu)-AAHDFVEWLLSA-NH2 (SEQ ID NO: 47);

H-HGEGTFTSDYSKYLDSK(hexadecanoyl-isoGlu)-AAHDFVEWLLSA-NH2 (SEQ ID NO: 48);

H-HSQ-Aib-TFTSDYSKYLDSK(hexadecanoyl-isoGlu)-AAHDFVEWLLSA-NH2 (SEQ ID NO: 49);

H-H-Aib-QLTFTSDYSKYLDSK(hexadecanoyl-isoGlu)-AAHDFVEWLLSA-NH2 (SEQ ID NO: 50);

H-H-Aib-QPTFTSDYSKYLDSK(hexadecanoyl-isoGlu)-AAHDFVEWLLSA-NH2 (SEQ ID NO: 51);
```

-continued

H-H-Aib-QETFTSDYSKYLDSK(hexadecanoyl-isoGlu)-AAHDFVEWLLSA-NH$_2$ (SEQ ID NO: 52);

H-H-Aib-Q-Aib-TFTSDYSKYLDSK(hexadecanoyl-isoGlu)-AAHDFVEWLLSA-NH$_2$ (SEQ ID NO: 53);

H-H-Aib-QFTFTSDYSKYLDSK(hexadecanoyl-isoGlu)-AAHDFVEWLLSA-NH$_2$ (SEQ ID NO: 54);

H-H-Aib-FGTFTSDYSKYLDSK(hexadecanoyl-isoGlu)-AAHDFVEWLLSA-NH$_2$ (SEQ ID NO: 55);

H-H-Aib-Q-DPhe-TFTSDYSKYLDSK(hexadecanoyl-isoGlu)-AAHDFVEWLLSA-NH$_2$ (SEQ ID NO: 56);

H-H-Aib-QRTFTSDYSKYLDSK(hexadecanoyl-isoGlu)-AAHDFVEWLLSA-NH$_2$ (SEQ ID NO: 57);

H-H-Aib-LGTFTSDYSKYLDSK(hexadecanoyl-isoGlu)-AAHDFVEWLLSA-NH$_2$ (SEQ ID NO: 58);

H-H-Aib-Hph-GTFTSDYSKYLDSK(hexadecanoyl-isoGlu)-AAHDFVEWLLSA-NH$_2$ (SEQ ID NO: 59);

H-H-Aib-WGTFTSDYSKYLDSK(hexadecanoyl-isoGlu)-AAHDFVEWLLSA-NH$_2$ (SEQ ID NO: 60);

H-H-Aib-YGTFTSDYSKYLDSK(hexadecanoyl-isoGlu)-AAHDFVEWLLSA-NH$_2$ (SEQ ID NO: 61);

H-H-Aib-VGTFTSDYSKYLDSK(hexadecanoyl-isoGlu)-AAHDFVEWLLSA-NH$_2$ (SEQ ID NO: 62);

H-H-Aib-QKTFTSDYSKYLDSK(hexadecanoyl-isoGlu)-AAHDFVEWLLSA-NH$_2$ (SEQ ID NO: 63);

H-H-Aib-RGTFTSDYSKYLDSK(hexadecanoyl-isoGlu)-AAHDFVEWLLSA-NH$_2$ (SEQ ID NO: 64);

H-H-Aib-AGTFTSDYSKYLDSK(hexadecanoyl-isoGlu)-AAHDFVEWLLSA-NH$_2$ (SEQ ID NO: 65);

H-H-Aib-SGTFTSDYSKYLDSK(hexadecanoyl-isoGlu)-AAHDFVEWLLSA-NH$_2$ (SEQ ID NO: 66);

H-H-Aib-IGTFTSDYSKYLDSK(hexadecanoyl-isoGlu)-AAHDFVEWLLSA-NH$_2$ (SEQ ID NO: 67);

H-H-Aib-GGTFTSDYSKYLDSK(hexadecanoyl-isoGlu)-AAHDFVEWLLSA-NH$_2$ (SEQ ID NO: 68);

H-H-Aib-PGTFTSDYSKYLDSK(hexadecanoyl-isoGlu)-AAHDFVEWLLSA-NH$_2$ (SEQ ID NO: 69);

H-H-Aib-HGTFTSDYSKYLDSK(hexadecanoyl-isoGlu)-AAHEFVEWLLEA-NH$_2$ (SEQ ID NO: 70);

H-H-Aib-Cit-GTFTSDYSKYLDSK(hexadecanoyl-isoGlu)-AAHDFVEWLLSA-NH$_2$ (SEQ ID NO: 71);

H-H-Aib-Q-DAla-TFTSDYSKYLDSK(hexadecanoyl-isoGlu)-AAHDFVEWLLSA-NH$_2$ (SEQ ID NO: 72);

H-H-Aib-Hse-GTFTSDYSKYLDSK(hexadecanoyl-isoGlu)-AAHDFVEWLLSA-NH$_2$ (SEQ ID NO: 73);

H-H-Aib-Q-DLeu-TFTSDYSKYLDSK(hexadecanoyl-isoGlu)-AAHDFVEWLLSA-NH$_2$ (SEQ ID NO: 74);

H-H-Aib-HGTFTSDYSKYLESK(hexadecanoyl-isoGlu)-AAEEFVEWLLEA-NH$_2$ (SEQ ID NO: 75);

H-H-Aib-1Nal-GTFTSDYSKYLDSK(hexadecanoyl-isoGlu)-AAHDFVEWLLSA-NH$_2$ (SEQ ID NO: 76);

H-H-Aib-[3-(2-furyl)alanyl]-GTFTSDYSKYLDSK(hexadecanoyl-isoGlu)-AAHDFVEWLLSA-NH$_2$ (SEQ ID NO: 77);

H-H-Aib-[3-(4-thiazolyl)alanyl]-GTFTSDYSKYLDSK(hexadecanoyl-isoGlu)-AAHDFVEWLLSA-NH$_2$ (SEQ ID NO: 78);

H-H-Aib-[3-(3-pyridyl)alanyl]-GTFTSDYSKYLDSK(hexadecanoyl-isoGlu)-AAHDFVEWLLSA-NH$_2$ (SEQ ID NO: 79);

H-H-Aib-[3-(4-pyridyl)alanyl]-GTFTSDYSKYLDSK(hexadecanoyl-isoGlu)-AAHDFVEWLLSA-NH$_2$ (SEQ ID NO: 80);

H-H-Aib-[3-(2-thienyl)alanyl]-GTFTSDYSKYLDSK(hexadecanoyl-isoGlu)-AAHDFVEWLLSA-NH$_2$ (SEQ ID NO: 81);

H-H-Aib-[3-(3-thienyl)alanyl]-GTFTSDYSKYLDSK(hexadecanoyl-isoGlu)-AAHDFVEWLLSA-NH$_2$ (SEQ ID NO: 82);

H-H-Aib-[3-(1-pyrazolyl)alanyl]-GTFTSDYSKYLDSK(hexadecanoyl-isoGlu)-AAHDFVEWLLSA-NH$_2$ (SEQ ID NO: 83); or H-H-Aib-[3-(1,2,4-triazol-1-yl)alanyl]-GTFTSDYSKYLDSK(hexadecanoyl-isoGlu)-AAHDFVEWLLSA-NH$_2$ (SEQ ID NO: 84).

Each of the latter compounds, independently, constitutes an individual embodiment of a compound of the invention.

Among preferred examples of individual compounds of the invention [in all of which the N-terminal group $R^1$ is hydrogen (H) and the C-terminal group $R^2$ is an amino group (NH$_2$)] are the following:

H-H-Aib-HGTFTSDYSKYLDSK(hexadecanoyl-isoGlu)-AAHDFVEWLLSA-NH$_2$ (SEQ ID NO: 44);

H-HGEGTFTSDYSKYLDSK(hexadecanoyl-isoGlu)-AAHDFVEWLLSA-NH$_2$ (SEQ ID NO: 48);

-continued

H-H-Aib-QLTFTSDYSKYLDSK(hexadecanoyl-isoGlu)-AAHDFVEWLLSA-NH$_2$ (SEQ ID NO: 50);

H-H-Aib-FGTFTSDYSKYLDSK(hexadecanoyl-isoGlu)-AAHDFVEWLLSA-NH$_2$ (SEQ ID NO: 55);

H-H-Aib-Q-DPhe-TFTSDYSKYLDSK(hexadecanoyl-isoGlu)-AAHDFVEWLLSA-NH$_2$ (SEQ ID NO: 56);

H-H-Aib-LGTFTSDYSKYLDSK(hexadecanoyl-isoGlu)-AAHDFVEWLLSA-NH$_2$ (SEQ ID NO: 58);

H-H-Aib-YGTFTSDYSKYLDSK(hexadecanoyl-isoGlu)-AAHDFVEWLLSA-NH$_2$ (SEQ ID NO: 61);

H-H-Aib-VGTFTSDYSKYLDSK(hexadecanoyl-isoGlu)-AAHDFVEWLLSA-NH$_2$ (SEQ ID NO: 62);

H-H-Aib-AGTFTSDYSKYLDSK(hexadecanoyl-isoGlu)-AAHDFVEWLLSA-NH$_2$ (SEQ ID NO: 65);

H-H-Aib-SGTFTSDYSKYLDSK(hexadecanoyl-isoGlu)-AAHDFVEWLLSA-NH$_2$ (SEQ ID NO: 66);

H-H-Aib-IGTFTSDYSKYLDSK(hexadecanoyl-isoGlu)-AAHDFVEWLLSA-NH$_2$ (SEQ ID NO: 67);

H-H-Aib-GGTFTSDYSKYLDSK(hexadecanoyl-isoGlu)-AAHDFVEWLLSA-NH$_2$ (SEQ ID NO: 68);

H-H-Aib-PGTFTSDYSKYLDSK(hexadecanoyl-isoGlu)-AAHDFVEWLLSA-NH$_2$ (SEQ ID NO: 69);

H-H-Aib-HGTFTSDYSKYLDSK(hexadecanoyl-isoGlu)-AAHEFVEWLLEA-NH$_2$ (SEQ ID NO: 70);

H-H-Aib-Cit-GTFTSDYSKYLDSK(hexadecanoyl-isoGlu)-AAHDFVEWLLSA-NH$_2$ (SEQ ID NO: 71);

H-H-Aib-Q-DAla-TFTSDYSKYLDSK(hexadecanoyl-isoGlu)-AAHDFVEWLLSA-NH$_2$ (SEQ ID NO: 72);

H-H-Aib-Hse-GTFTSDYSKYLDSK(hexadecanoyl-isoGlu)-AAHDFVEWLLSA-NH$_2$ (SEQ ID NO: 73);

H-H-Aib-Q-DLeu-TFTSDYSKYLDSK(hexadecanoyl-isoGlu)-AAHDFVEWLLSA-NH$_2$ (SEQ ID NO: 74);

H-H-Aib-HGTFTSDYSKYLESK(hexadecanoyl-isoGlu)-AAEEFVEWLLEA-NH$_2$ (SEQ ID NO: 75);

H-H-Aib-[3-(2-furyl)alanyl]-GTFTSDYSKYLDSK(hexadecanoyl-isoGlu)-AAHDFVEWLLSA-NH$_2$ (SEQ ID NO: 77);

H-H-Aib-[3-(4-thiazolyl)alanyl]-GTFTSDYSKYLDSK(hexadecanoyl-isoGlu)-AAHDFVEWLLSA-NH$_2$ (SEQ ID NO: 78);

H-H-Aib-[3-(3-pyridyl)alanyl]-GTFTSDYSKYLDSK(hexadecanoyl-isoGlu)-AAHDFVEWLLSA-NH$_2$ (SEQ ID NO: 79);

H-H-Aib-[3-(2-thienyl)alanyl]-GTFTSDYSKYLDSK(hexadecanoyl-isoGlu)-AAHDFVEWLLSA-NH$_2$ (SEQ ID NO: 81);

H-H-Aib-[3-(3-thienyl)alanyl]-GTFTSDYSKYLDSK(hexadecanoyl-isoGlu)-AAHDFVEWLLSA-NH$_2$ (SEQ ID NO: 82);

H-H-Aib-[3-(1-pyrazolyl)alanyl]-GTFTSDYSKYLDSK(hexadecanoyl-isoGlu)-AAHDFVEWLLSA-NH$_2$ (SEQ ID NO: 83);
or H-H-Aib-[3-(1,2,4-triazol-1-yl)alanyl]-GTFTSDYSKYLDSK(hexadecanoyl-isoGlu)-AAHDFVEWLLSA-NH$_2$ (SEQ ID NO: 84).

As before, each of the latter compounds, independently, constitutes an individual embodiment of a compound of the invention.

One group of preferred examples of individual compounds of the invention is the following:

H-H-Aib-HGTFTSDYSKYLDSK(hexadecanoyl-isoGlu)-AAHDFVEWLLSA-NH$_2$ (SEQ ID NO: 44);

H-H-Aib-IGTFTSDYSKYLDSK(hexadecanoyl-isoGlu)-AAHDFVEWLLSA-NH$_2$ (SEQ ID NO: 67);

H-H-Aib-Q-DPhe-TFTSDYSKYLDSK(hexadecanoyl-isoGlu)-AAHDFVEWLLSA-NH$_2$ (SEQ ID NO: 56);

H-H-Aib-YGTFTSDYSKYLDSK(hexadecanoyl-isoGlu)-AAHDFVEWLLSA-NH$_2$ (SEQ ID NO: 61);

H-H-Aib-PGTFTSDYSKYLDSK(hexadecanoyl-isoGlu)-AAHDFVEWLLSA-NH$_2$ (SEQ ID NO: 69);

H-H-Aib-HGTFTSDYSKYLDSK(hexadecanoyl-isoGlu)-AAHEFVEWLLEA-NH$_2$ (SEQ ID NO: 70);

H-H-Aib-Q-DAla-TFTSDYSKYLDSK(hexadecanoyl-isoGlu)-AAHDFVEWLLSA-NH$_2$ (SEQ ID NO: 72);

H-H-Aib-Hse-GTFTSDYSKYLDSK(hexadecanoyl-isoGlu)-AAHDFVEWLLSA-NH$_2$ (SEQ ID NO: 73);

H-H-Aib-Q-DLeu-TFTSDYSKYLDSK(hexadecanoyl-isoGlu)-AAHDFVEWLLSA-NH$_2$ (SEQ ID NO: 74);

H-H-Aib-HGTFTSDYSKYLESK(hexadecanoyl-isoGlu)-AAEEFVEWLLEA-NH$_2$ (SEQ ID NO: 75);

H-H-Aib-[3-(4-thiazolyl)alanyl]-GTFTSDYSKYLDSK(hexadecanoyl-isoGlu)-AAHDFVEWLLSA-NH$_2$ (SEQ ID NO: 78);

```
H-H-Aib-[3-(3-pyridyl)alanyl]-GTFTSDYSKYLDSK(hexadecanoyl-isoGlu)-AAHDFVEWLLSA-NH₂ (SEQ ID NO: 79);

H-H-Aib-[3-(2-thienyl)alanyl]-GTFTSDYSKYLDSK(hexadecanoyl-isoGlu)-AAHDFVEWLLSA-NH₂ (SEQ ID NO: 81);

H-H-Aib-[3-(3-thienyl)alanyl]-GTFTSDYSKYLDSK(hexadecanoyl-isoGlu)-AAHDFVEWLLSA-NH₂ (SEQ ID NO: 82);
and H-H-Aib-[3-(1,2,4-triazol-1-yl)alanyl]-GTFTSDYSKYLDSK(hexadecanoyl-isoGlu)-AAHDFVEWLLSA-NH₂ (SEQ ID NO: 84).
```

Another group of preferred examples of individual compounds of the invention is the following:

```
H-HGEGTFTSDYSKYLDSK(hexadecanoyl-isoGlu)-AAHDFVEWLLSA-NH₂ (SEQ ID NO: 48);

H-H-Aib-LGTFTSDYSKYLDSK(hexadecanoyl-isoGlu)-AAHDFVEWLLSA-NH₂ (SEQ ID NO: 58);

H-H-Aib-VGTFTSDYSKYLDSK(hexadecanoyl-isoGlu)-AAHDFVEWLLSA-NH₂ (SEQ ID NO: 62);

H-H-Aib-AGTFTSDYSKYLDSK(hexadecanoyl-isoGlu)-AAHDFVEWLLSA-NH₂ (SEQ ID NO: 65);

H-H-Aib-SGTFTSDYSKYLDSK(hexadecanoyl-isoGlu)-AAHDFVEWLLSA-NH₂ (SEQ ID NO: 66);

H-H-Aib-GGTFTSDYSKYLDSK(hexadecanoyl-isoGlu)-AAHDFVEWLLSA-NH₂ (SEQ ID NO: 68);

H-H-Aib-Cit-GTFTSDYSKYLDSK(hexadecanoyl-isoGlu)-AAHDFVEWLLSA-NH₂ (SEQ ID NO: 71);

H-H-Aib-[3-(1-pyrazolyl)alanyl]-GTFTSDYSKYLDSK(hexadecanoyl-isoGlu)-AAHDFVEWLLSA-NH₂ (SEQ ID NO: 83);
and H-H-Aib-[3-(2-furyl)alanyl]-GTFTSDYSKYLDSK(hexadecanoyl-isoGlu)-AAHDFVEWLLSA-NH₂ (SEQ ID NO: 77).
```

As before, the individual compounds in each of the latter two groups of compounds each constitute an individual embodiment of a compound of the invention.

Compositions (notably pharmaceutical compositions) of the invention may further be compounded in, or attached to, for example through covalent, hydrophobic and electrostatic interactions, a drug carrier, drug delivery system or advanced drug delivery system in order to further enhance stability of the compound of the invention, to increase bioavailability, to increase solubility, to decrease adverse effects, to achieve chronotherapy well known to those skilled in the art, or to increase patient compliance, or any combination thereof. Examples of carriers, drug delivery systems and advanced drug delivery systems include, but are not limited to, polymers, for example: cellulose and derivatives; polysaccharides, for example dextran and derivatives; starch and derivatives; poly(vinyl alcohol); acrylate and methacrylate polymers; polylactic and polyglycolic acid, and block co-polymers thereof; polyethylene glycols; carrier proteins, for example albumin; gels, for example thermogelling systems, for example block co-polymeric systems well known to those skilled in the art; micelles; liposomes; microspheres; nanoparticulates; liquid crystals and dispersions thereof; L2 phase and dispersions thereof well known to those skilled in the art of phase behaviour in lipid-water systems; polymeric micelles; multiple emulsions, self-emulsifying, self-microemulsifying; cyclodextrins and derivatives thereof; and dendrimers.

Attempts have been made previously to prolong the half-life of Glucagon/GLP-1 dual receptor agonist compounds by derivatisation with polyethylene glycol (PEG) (see WO2008/101017). However such derivatisation appears to be most effective when applied to the C-terminus of the molecule rather than in the central core of the peptide backbone, and potency of such compounds appears to be generally decreased compared to that of the corresponding unmodified peptides.

The presence of basic amino acid residues at positions 17 and 18 (both of which are Arg residues in native glucagon) is generally believed to be necessary for full glucagon receptor activation (Unson et al. J. Biol. Chem. 1998, 273, 10308-10312). However, within the framework of the present invention it appears that when the amino acid residue in position 18 is alanine, substitution with a hydrophobic amino acid residue in position 17 may still yield a highly potent compound; this applies even in the case of compounds of the invention in which the amino acid residue in position 17 is derivatized with a lipophilic substituent, in that such compounds may retain high potency at both glucagon and GLP-1 receptors, but may also display a significantly protracted pharmacokinetic profile. This may be the case even when a lysine residue in position 17 is derivatized, converting the basic amine side-chain into a neutral amide group.

Peptide Synthesis

The peptide component of the compounds of the invention may be manufactured by standard synthetic methods, by using recombinant expression systems, or by any other suitable method. Thus the peptides may be synthesized in a number of ways, including, for example, methods which comprise:

(a) synthesising the peptide by means of solid-phase or liquid-phase methodology, either stepwise or by fragment assembly, and isolating and purifying the final peptide product; or (b) expressing a nucleic acid construct that encodes the peptide in a host cell, and recovering the expression product from the host cell culture; or (c) effecting cell-free in vitro expression of a nucleic acid construct that encodes the peptide, and recovering the expression product;

or employing any combination of methods as in (a), (b) and (c) to obtain fragments of the peptide, subsequently ligating the fragments to obtain the complete peptide, and recovering the peptide.

It may often be preferable to synthesize compounds of the invention by means of solid-phase or liquid-phase peptide synthesis, the methodology of which is well known to persons of ordinary skill in the art of peptide synthesis. Reference may also be made in this respect to, for example, WO 98/11125 and Fields, G. B. et al., 2002, *"Principles and practice of solid-phase peptide synthesis"*. In: Synthetic Peptides (2nd Edition) and examples provided therein.

Lipophilic Substituents

A side-chain of an amino acid residue in one of several sequence positions (positions 17, 20, 24, 27 and/or 28, such as position 17) of a compound of the invention may, as already discussed, be conjugated to a lipophilic moiety $Z^1$, either directly or via a spacer group $Z^2$ Without wishing to be bound by any particular theory, it is thought that the lipophilic substituent (moiety) binds albumin in the blood stream, thereby shielding the compound from enzymatic degradation with attendant enhancement of the half-life of the compound. The presence of such a lipophilic moiety may also modulate the potency of the compound, e.g. with respect to the glucagon receptor and/or the GLP-1 receptor.

The term "conjugated" is used here to describe the linking or attachment of one identifiable chemical moiety to another, and the structural relationship between such moieties. It should not be taken to imply any particular method of synthesis.

The spacer $Z^2$, when present, serves to provide a spacing between the lipophilic moiety $Z^1$ and the amino acid residue in question of the compound of the invention.

The lipophilic substituent may, by way of example, suitably be attached to the amino acid side-chain or to the intervening spacer moiety via an ester, a sulfonyl ester, a thioester, an amide or a sulfonamide functionality. Accordingly, it will be understood that the lipophilic substituent preferably comprises an acyl group or a sulfonyl group, or an N atom, an O atom or an S atom which forms part of the ester, sulfonyl ester, thioester, amide or sulfonamide. It is preferable that an acyl group in the lipophilic substituent forms part of an amide or ester with the amino acid side-chain or the spacer.

As already indicated above, the lipophilic substituent or moiety may comprise a hydrocarbon chain having from 10 to 24 C atoms, e.g. from 10 to 22 C atoms, such as from 10 to 20 C atoms. It will often preferably have at least 11 C atoms, and preferably have 18 C atoms or less. For example, the hydrocarbon chain may contain 12, 13, 14, 15, 16, 17 or 18 carbon atoms. The hydrocarbon chain may be linear or branched, and may be saturated or unsaturated. From the discussion above it will be understood that the hydrocarbon chain is preferably substituted with a moiety which forms part of the covalent attachment to an amino acid side-chain or the spacer, for example an acyl group, a sulfonyl group, an N atom, an O atom or an S atom. Most preferably the hydrocarbon chain is substituted with an acyl group, and accordingly the hydrocarbon chain may be part of an alkanoyl group, for example a dodecanoyl, tridecanoyl, 2-butyloctanoyl, tetradecanoyl, pentadecanoyl, hexadecanoyl, heptadecanoyl, octadecanoyl or eicosanoyl group.

As already mentioned, the lipophilic substituent $Z^1$ may be conjugated to the amino acid side-chain in question by a spacer $Z^2$. When present, the spacer is covalently attached (bonded) to the lipophilic substituent and to the amino acid side-chain. The spacer may be attached to the lipophilic substituent and to the amino acid side-chain, independently, by means of an ester, a sulfonyl ester, a thioester, an amide or a sulphonamide functionality. Accordingly, the spacer may comprise two moieties independently selected from acyl, sulfonyl, an N atom, an O atom and an S atom. The spacer $Z^2$ may consist of a linear $C_{1-10}$ hydrocarbon chain, more preferably a linear $C_{1-5}$ hydrocarbon chain. It may optionally further be substituted with one or more substituents selected from $C_{1-6}$alkyl, $C_{1-6}$alkyl amine, $C_{1-6}$alkyl hydroxy and $C_{1-6}$alkyl carboxy.

Alternatively, the spacer $Z^2$ may be, for example, a residue of any naturally occurring or non-naturally occurring amino acid. For example, the spacer may be a residue of Gly, Pro, Ala, Val, Leu, Ile, Met, Cys, Phe, Tyr, Trp, His, Lys, Arg, Gln, Asn, α-Glu, γ-Glu (also termed isoGlu), ε-Lys, Asp, Ser, Thr, Gaba, Aib, β-Ala (i.e. 3-aminopropanoyl), 4-aminobutanoyl, 5-aminopentanoyl, 6-aminohexanoyl, 7-aminoheptanoyl, 8-aminooctanoyl, 9-aminononanoyl, 10-aminodecanoyl or 8-amino-3,6-dioxaoctanoyl. In certain embodiments, the spacer is a residue of Glu, γ-Glu, ε-Lys, β-Ala (i.e. 3-aminopropanoyl), 4-aminobutanoyl, 8-aminooctanoyl or 8-amino-3,6-dioxaoctanoyl.

The amino acid side-chain to which a lipophilic substituent may be conjugated is a side-chain of a Glu, Lys, Ser or Cys residue, for example a side-chain of a Lys, Glu or Cys residue. Where two or more amino acid residue side-chains carry a lipophilic substituent, they may be independently selected from these residues. Thus, the amino acid side-chain may comprise a carboxy, hydroxy, thiol, amide or amine group, for forming an ester, sulfonyl ester, thioester, amide or sulphonamide linkage with the spacer or the lipophilic substituent.

An example of a lipophilic substituent comprising a lipophilic moiety $Z^1$ and a spacer $Z^2$ is shown below:

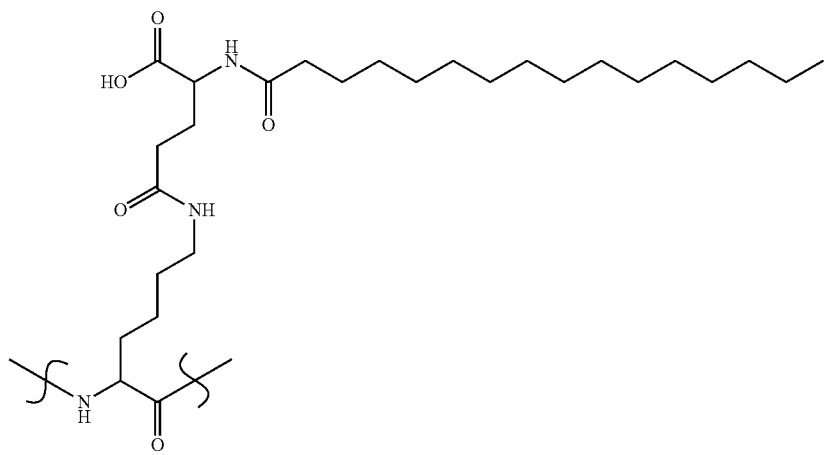 [SMILES: CCCCCCCCCCCCCCCC(=O)NC(CCC(=O)NCCCCC(NCC)C(=O)CC)C(=O)O]

In the above example, the side-chain of a Lys residue of the peptide of formula I is covalently attached to a γ-Glu spacer ($Z^2$) via an amide linkage, and a hexadecanoyl group ($Z^1$) is covalently attached to the γ-Glu spacer, likewise via an amide linkage. This combination of lipophilic moiety and spacer, conjugated to a Lys residue, may be referred to by the shorthand notation K(hexadecanoyl-γ-Glu) [or K(hexadecanoyl-isoGlu)], e.g. when shown in formulae of specific compounds of the present invention. As the moiety γ-Glu may (as already mentioned) also be referred to as isoGlu, and a hexadecanoyl group may also be referred to as a palmitoyl group, it will be apparent that the notation (hexadecanoyl-γ-Glu) is equivalent, inter alia, to the notations (isoGlu(Palm)) or (isoGlu(Palmitoyl)), as used for example in PCT/GB2008/004121.

The skilled person will be well aware of suitable techniques for preparing the compounds of the invention. For examples of suitable chemistry, see WO98/08871, WO00/55184, WO00/55119, Madsen et al (J. Med. Chem. 2007, 50, 6126-32), and Knudsen et al. 2000 (J. Med Chem. 43, 1664-1669).

Efficacy

Binding of a compound to GLP-1 or glucagon (glu) receptors may be used as an indication of agonist activity, but in general it is preferred to use a biological assay which measures intracellular signalling caused by binding of the compound to the relevant receptor. For example, activation of the glucagon receptor by a glucagon agonist will stimulate cellular cyclic AMP (cAMP) formation. Similarly, activation of the GLP-1 receptor by a GLP-1 agonist will stimulate cellular cAMP formation. Thus, production of cAMP in suitable cells expressing one of these two receptors can be used to monitor the relevant receptor activity. Use of a suitable pair of cell types, one expressing the GLP-1 receptor and the other expressing the glucagon receptor, can hence be used to determine agonist activity towards both types of receptor.

The skilled person will be aware of suitable assay formats, and examples are provided below. The GLP-1 receptor and/or the glucagon receptor may have the sequence of the receptors as described in the examples. For example, the assays may make use of the human glucagon receptor (glucagon-R) having primary accession number GI:4503947 (NP_000151.1) and/or the human glucagon-like peptide 1 receptor (GLP-1R) having primary accession number GI:166795283 (NP_002053.3). It should be understood in this connection that when sequences of precursor proteins are referred to, assays may make use of the mature protein, lacking the signal sequence.

$EC_{50}$ values may be used as a numerical measure of agonist potency at a given receptor. An $EC_{50}$ value is a measure of the concentration of a compound required to achieve half of that compound's maximal activity in a particular assay. Thus, by way of example, a compound having an $EC_{50}$ [GLP-1R] value lower than the $EC_{50}$ [GLP-1R] value for native glucagon in a particular assay may be considered to have higher potency at the GLP-1 receptor than glucagon itself.

Compounds of the invention as described herein are typically at least GLP-1 receptor agonists, i.e. they are capable of stimulating cAMP formation in cells expressing the GLP-1 receptor (GLP-1R), while certain compounds of the invention are glucagon/GLP-1 receptor dual agonists, i.e. they are capable of stimulating cAMP formation in cells expressing the glucagon receptor (glu-R) and in cells expressing the GLP-1 receptor (GLP-1R). The stimulation of each receptor can be measured in independent assays and subsequently compared. By comparing the $EC_{50}$ value for activity towards the glucagon receptor ($EC_{50}$ [glucagon-R]) with the $EC_{50}$ value for activity towards the GLP-1 receptor ($EC_{50}$ [GLP-1R]) for a given compound, the relative glucagon receptor selectivity (%) of that compound may be determined as follows:

Relative glu-R selectivity=(1/$EC_{50}$[glucagon-R])×100%/(1/$EC_{50}$[glucagon-R]+1/$EC_{50}$[GLP-1R])

The relative GLP-1 receptor selectivity (%) of the compound may correspondingly be determined as follows:

Relative GLP-1R selectivity=(1/$EC_{50}$[GLP-1R])×100%/(1/$EC_{50}$[glucagon-R]+1/$EC_{50}$[GLP-1R])

A compound's relative selectivity allows its effect on the GLP-1 receptor and the glucagon receptor, respectively, to be compared directly. For example, the higher the relative GLP-1 selectivity of a given compound is, the more effective is that compound towards the GLP-1 receptor compared to the glucagon receptor.

Using the assays described below, the relative GLP-1 selectivity for human glucagon has been determined to be approximately 5%.

Compounds of the invention generally have a higher relative GLP-1R selectivity than human glucagon. Thus, for a particular level of glucagon receptor (glu-R) agonist activity, the compounds will generally display a higher level of GLP-1R agonist activity (i.e. greater potency at the GLP-1 receptor) than glucagon. It will be understood that the absolute potency of a particular compound at the glucagon and GLP-1 receptors may be higher than, lower than or approximately equal to that of native human glucagon, as long as the appropriate relative GLP-1R selectivity is achieved.

Nevertheless, certain compounds of the invention may have a lower $EC_{50}$ [GLP-1R] value than human glucagon. Certain compounds may further have a lower $EC_{50}$ [GLP-1R] value than glucagon while maintaining an $EC_{50}$ [glucagon-R] value that is less than 10-fold higher than that for human glucagon, e.g. less than 5-fold higher than that for human glucagon, or even less than 2-fold higher than that for human glucagon.

It some instances it may be desirable that $EC_{50}$ for a given compound towards both the glu-R and GLP-1R should be less than about 2 nM, such as about 1 nM, or less than 1 nM.

Certain compounds of the invention may have a $EC_{50}$ [glucagon-R] value that is less than approx. 10-fold higher than that for human glucagon, e.g. less than approx. 5-fold higher, such as less than 2-fold higher than that for human glucagon. Certain compounds may further have a $EC_{50}$ [glucagon-R] value that is less than approx. 10-fold higher than that for human glucagon, e.g. less than approx. 5-fold higher, such as less than 2-fold higher than that for human glucagon, while having a $EC_{50}$ [GLP-1R] value that is at approx. equal to, or less than, that for human glucagon, such as less than half that for human glucagon, e.g. less than a fifth of that for human glucagon, or even less than a tenth of that for human glucagon.

The relative GLP-1R selectivity of the compounds may be greater than 5% and less than 100%, such as greater than 5% and less than 95%. For example, the compounds may have a relative GLP-1R selectivity of 5-20%, 10-30%, 20-50%, 30-70% or 50-80%, or of 30-50%, 40-60%, 50-70% or 75-95%.

Therapeutic Uses

Compounds of the invention may provide an attractive option for treatment of, inter alia, metabolic diseases, including obesity and diabetes mellitus (diabetes).

Diabetes comprises a group of metabolic diseases characterized by hyperglycemia resulting from defects in insulin secretion, insulin action, or both. Acute signs of diabetes include excessive urine production, resulting compensatory thirst and increased fluid intake, blurred vision, unexplained weight loss, lethargy, and changes in energy metabolism. The chronic hyperglycemia of diabetes is associated with long-term damage to, and dysfunction and failure of, various organs, notably the eyes, kidneys, nerves, heart and blood vessels. Diabetes is classified into type 1 diabetes, type 2 diabetes and gestational diabetes on the basis on pathogenetic characteristics.

Type 1 diabetes accounts for about 5-10% of all diabetes cases, and is believed to be caused by auto-immune destruction of insulin-secreting pancreatic β-cells.

Type 2 diabetes accounts for about 90-95% of diabetes cases, and is a result of a complex set of metabolic disorders. Type 2 diabetes is the consequence of endogenous insulin production becoming insufficient to maintain plasma glucose levels below the diagnostic thresholds.

Gestational diabetes refers to any degree of glucose intolerance identified during pregnancy.

Pre-diabetes includes impaired fasting glucose and impaired glucose tolerance, and refers to those states that occur when blood glucose levels are elevated, but are still below levels that are established for the clinical diagnosis for diabetes.

A large proportion of people with type 2 diabetes and pre-diabetes are at increased risk of morbidity and mortality due to the high prevalence of additional metabolic risk factors, including abdominal obesity (excessive fat tissue around the abdominal internal organs), atherogenic dyslipidemia (blood fat disorders, including high triglyceride levels, low HDL cholesterol and/or high LDL cholesterol levels, which foster plaque build-up in arterial walls), elevated blood pressure (hypertension), prothrombotic states (e.g. high fibrinogen or plasminogen activator inhibitor-1 levels in the blood) and proinflammatory states (e.g. elevated C-reactive protein levels in the blood).

Conversely, obesity confers an increased risk of developing pre-diabetes, type 2 diabetes as well as, e.g., certain types of cancer, obstructive sleep apnea and gall-bladder disease.

Dyslipidaemia is associated with increased risk of cardiovascular disease. High Density Lipoprotein (HDL) is of clinical importance since an inverse correlation exists between plasma HDL concentrations and risk of atherosclerotic disease. The major part of cholesterol stored in atherosclerotic plaques originates from Low Density Lipoprotein (LDL), and hence elevated LDL levels are closely associated with atherosclerosis. The HDL/LDL ratio is a clinical risk indicator for atherosclerosis and coronary atherosclerosis, in particular.

Without wishing to be bound by any particular theory, it is believed that compounds of the invention that act as glucagon/GLP-1 receptor dual agonists may combine the physiological effect of glucagon, e.g. on fat metabolism, with the physiological effect of GLP-1, e.g. on blood glucose levels and food intake. They may therefore act to accelerate elimination of excess adipose tissue, induce sustainable weight loss, and improve glycemic control. Glucagon/GLP-1 receptor dual agonists may also act to reduce cardiovascular risk factors, such as high cholesterol and LDL-cholesterol levels.

Compounds of the present invention may therefore be of value as pharmaceutical agents for preventing weight gain, promoting weight loss, reducing excess body weight or treating obesity (e.g. by control of appetite, feeding, food intake, calorie intake, and/or energy expenditure), including morbid obesity, as well as for treating associated diseases and health conditions, including, but not limited to, obesity-linked inflammation, obesity-linked gallbladder disease and obesity-induced sleep apnea. Compounds of the invention may also be useful for treatment of insulin resistance, glucose intolerance, pre-diabetes, increased fasting glucose, type 2 diabetes, hypertension, dyslipidemia (or a combination of these metabolic risk factors), atherosclerois, arteriosclerosis, coronary heart disease, peripheral artery disease and stroke. These are all conditions which can be associated with obesity. However, the effects of compounds of the invention on these conditions may be mediated in whole or in part via an effect on body weight, or may be independent thereof.

Pharmaceutical Compositions

Compounds of the present invention, or pharmaceutically acceptable salts thereof, may be formulated as pharmaceutical compositions, suitable for storage or intended for essentially immediate administration, and typically comprising a therapeutically effective amount of a compound of the invention, or pharmaceutically acceptable salt thereof, in a pharmaceutically acceptable carrier.

The therapeutically effective amount of a compound of the present invention will depend on the route of administration, the subject (human or animal) to be treated, and the physical characteristics of the subject in question. These factors and their relationship in determining a therapeutically effective amount are well known to skilled practitioners in the medical arts. The amount in question and the method of administration can be tailored to achieve optimal efficacy, and may depend on such factors as weight, diet, possible concurrent medication and other factors well known to those skilled in the medical arts. The dosage sizes and dosing regimen most appropriate for human use may be guided by results obtained in the context of the present invention, and may be confirmed in properly designed clinical trials.

An effective dosage and treatment protocol may be determined by conventional means, starting with a low dose in laboratory animals and then increasing the dosage while monitoring the effects and systematically varying the dosage regimen. Numerous factors may be taken into consideration by a clinician when determining an optimal dosage for a given subject. Such considerations are known to the skilled person.

The term "pharmaceutically acceptable carrier" includes any of the standard pharmaceutical carriers or diluents, such as those used in formulations suitable for oral, rectal, nasal or parenteral (including subcutaneous, intramuscular, intravenous, intradermal and transdermal) administration. Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). For example, sterile saline or phosphate-buffered saline (PBS) at slightly acidic or physiological pH may be used. Among appropriate pH-buffering agents are phosphates, citrate, acetate, tris/hydroxymethyl)aminomethane (TRIS), N-Tris(hydroxymethyl)methyl-3-aminopropane-sulfonic acid (TAPS), ammonium bicarbonate, diethanolamine, histidine (which is often a preferred buffer), arginine, lysine and acetate, as well as mixtures thereof. The term further encompasses any agents listed in the US Pharmacopeia for use in animals or humans.

The term "pharmaceutically acceptable salt" in the context of the invention generally refers to a salt such as an acid addition salt or a basic salt. Examples of suitable acid addition salts include hydrochloride salts, citrate salts, acetate salts and trifluoroacetate salts. Examples of basic salts include salts where the cation is selected from alkali metal ions, such as sodium and potassium, alkaline earth metal ions, such as calcium, as well as substituted ammonium ions, e.g. of the type $NR(R')_3$, where R and R' independently designate optionally substituted $C_{1-6}$alkyl, optionally substituted $C_{2-6}$alkenyl, optionally substituted aryl, or optionally substituted heteroaryl. Other examples of pharmaceutically acceptable salts are described in *Remington's Pharmaceutical Sciences*, 17th edition. Ed. Alfonso R. Gennaro (Ed.), Mark Publishing Company, Easton, Pa., U.S.A., 1985 and more recent editions, and in the *Encyclopaedia of Pharmaceutical Technology*.

The term "treatment" as employed in the context of the invention refers to an approach for obtaining beneficial or desired clinical results. For the purposes of the present invention, beneficial or desired clinical results include, but are not limited to, alleviation of symptoms, diminishment of extent of disease, stabilization of (i.e. not worsening of) state of disease, delay or slowing of disease progression, amelioration or palliation of disease state, and remission (whether partial or total), whether detectable or undetectable. "Treatment" may also refer to prolongation of survival compared to expected survival in the absence of treatment. "Treatment" is an intervention performed with the intention of preventing the development of, or altering the pathology of, a disorder. Accordingly, "treatment" refers both to therapeutic treatment and to prophylactic or preventative measures. Those in need of treatment include those already suffering from the disorder, as well as those in which development of the disorder is to be prevented. "Treatment" also means inhibition or reduction of an increase in pathology or symptoms (e.g. weight gain or hyperglycaemia) compared to the absence of treatment, and is not necessarily meant to imply complete cessation of the relevant condition.

A pharmaceutical composition of the invention may be prepared by any of the methods well known in the art of pharmacy, and may, e.g., be in unit dosage form. In such form, the composition is divided into unit doses containing appropriate quantities of the active component. The unit dosage form may be a packaged preparation, the package containing discrete quantities of the preparation in question (for example, packeted tablets, capsules or powders in vials or ampoules). In certain embodiments, a packaged form may include a label or insert with instructions for use. The unit dosage form may also be a capsule, sachet or tablet itself, or it may be an appropriate number of any of these packaged forms. It may be provided in single-dose injectable form, for example in the form of a pen. Compositions may be formulated for any suitable route and means of administration. Subcutaneous or transdermal modes of administration may be among administration routes suitable for compounds of the invention.

Combination Therapy

Reference in the following to a compound of the invention also extends to a pharmaceutically acceptable salt or solvate thereof as well as to a composition comprising more than one different compound of the invention.

A compound of the invention may be administered as part of a combination therapy together with one or more other agents, e.g. agents useful for treatment of diabetes, obesity, dyslipidaemia or hypertension. In such cases, the active agents [i.e. compound(s) of the invention and other agent(s)] may be administered together or separately, as constituents of one and the same pharmaceutical formulation or as separate pharmaceutical formulations.

Thus, a compound of the invention (or a salt thereof) may be used in combination with a known anti-diabetic agent, including, but not limited to, metformin, a sulfonylurea, a glinide, a dipeptidylpeptidase IV (DPP-IV) inhibitor, a glitazone, or insulin. In a preferred embodiment the compound of the invention or salt thereof is used in combination with insulin, a DPP-IV inhibitor, a sulfonylurea or metformin, particularly a sulfonylurea or metformin, for achieving adequate glycemic control. In a more preferred embodiment, the compound of the invention or salt thereof is used in combination with a metformin, a sulfonylurea, insulin or an insulin analogue for achieving adequate glycemic control. Examples of insulin analogues include, but are not limited to, Lantus™, Novorapid™, Humalog™, Novomix™ Actraphane™ HM, Levemir™ and Apidra™.

A compound of the invention or salt thereof may further be used in combination with a known anti-obesity agent, including, but not limited to, a glucagon-like peptide 1 (GLP-1) receptor agonist, peptide YY or an analogue thereof, a cannabinoid receptor 1 antagonist, a lipase inhibitor, a melanocortin receptor 4 agonist, or a melanin concentrating hormone receptor 1 antagonist.

A compound of the invention or salt thereof may also be used in combination with a known anti-hypertension agent, including, but not limited to, an angiotensin-converting enzyme inhibitor, an angiotensin II receptor blocker, a diuretic, a beta-blocker, or a calcium channel blocker.

A compound of the invention or salt thereof may still further be used in combination with a known anti-dyslipidaemia agent, including, but not limited to, a statin, a fibrate, a niacin or a cholesterol absorption inhibitor.

Methods

Abbreviations employed are as follows:
ivDde: 1-(4,4-dimethyl-2,6-dioxocyclohexylidene)-3-methyl-butyl
Dde: 1-(4,4-dimethyl-2,6-dioxocyclohexylidene)-ethyl
DCM: dichloromethane
DMF: N,N-dimethylformamide
DIPEA: diisopropylethylamine
EtOH: ethanol
$Et_2O$: diethyl ether
HATU: N-[(dimethylamino)-1H-1,2,3-triazol[4,5-b]pyridine-1-ylmethylene]-N-methylmethanaminium hexafluorophosphate N-oxide
IBMX: 3-isobutyl-1-methylxanthine
MeCN: acetonitrile
NMP: N-methylpyrrolidone
TFA: trifluoroacetic acid
TIS: triisopropylsilane General Synthesis of Glucagon Analogues Solid-phase peptide synthesis was performed on a CEM Liberty Peptide Synthesizer using standard Fmoc chemistry. TentaGel S Ram resin (1 g; 0.25 mmol/g) was swelled in NMP (10 ml) prior to use and transferred between tube and reaction vessel using DCM and NMP.

Coupling:

An Fmoc-amino acid in NMP/DMF/DCM (1:1:1; 0.2 M; 5 ml) was added to the resin in a CEM Discover microwave unit together with HATU/NMP (0.5 M; 2 ml) and DIPEA/NMP (2.0 M; 1 ml). The coupling mixture was heated to 75° C. for 5 min while nitrogen was bubbled through the mixture. The resin was then washed with NMP (4×10 ml).

Deprotection:

Piperidine/NMP (20%; 10 ml) was added to the resin for initial deprotection and the mixture was heated by microwaves (30 sec.; 40° C.). The reaction vessel was drained and a second portion of piperidine/NMP (20%; 10 ml) was added and heated (75° C.; 3 min.) again. The resin was then washed with NMP (6×10 ml).

Amino Acid X Side-chain Derivitization (Acylation, with a Spacer $Z^2$ of the Amino Acid Type):

Fmoc-Lys(ivDde)-OH [or Fmoc-Lys(Dde)-OH], or another Fmoc-amino acid X with an orthogonal side-chain protective group, is introduced at the position of the acylation. The N-terminal of the peptide backbone is then Boc-protected using $Boc_2O$, or alternatively by using a Boc-protected amino acid in the last coupling. While the peptide is still attached to the resin, the orthogonal side-chain protective group is selectively cleaved using freshly prepared hydrazine hydrate (2-4%) in NMP for 2×15 min. The unprotected side-chain is first coupled with Fmoc-Glu-OtBu or another protected spacer amino acid, which is then deprotected with piperidine and acylated with a lipophilic moiety using the peptide coupling methodology as described above.

Cleavage:

The resin was washed with EtOH (3×10 ml) and Et$_2$O (3×10 ml) and dried to constant weight at room temperature (r.t.). The crude peptide was cleaved from the resin by treatment with TFA/TIS/water (95/2.5/2.5; 40 ml, 2 h; r.t.). Most of the TFA was removed under reduced pressure, and the crude peptide was precipitated and washed three times with diethyl ether and dried to constant weight at room temperature.

HPLC Purification of the Crude Peptide:

The crude peptide was purified to greater than 90% by preparative reverse-phase HPLC using a PerSeptive Biosystems VISION Workstation equipped with a C-18 column (5 cm; 10 μm) and a fraction collector, operated at 35 ml/min with a gradient of buffer A (0.1% TFA, aq.) and buffer B (0.1% TFA, 90% MeCN, aq.). Fractions were analysed by analytical HPLC and MS, and relevant fractions were pooled and lyophilised. The final product was characterised by HPLC and MS.

Generation of Cell Lines Expressing Human Glucagon Receptor and GLP-1 Receptor, Respectively cDNA encoding either the human glucagon receptor (glucagon-R) (primary accession number P47871) or the human glucagon-like peptide 1 receptor (GLP-1R) (primary accession number P43220) were cloned from the cDNA clones BC104854 (MGC:132514/IMAGE:8143857) and BC112126 (MGC:138331/IMAGE:8327594), respectively. The DNA encoding the glucagon-R or the GLP-1R was amplified by PCR using primers encoding terminal restriction sites for sub-cloning. The 5'-end primers additionally encoded a near Kozak consensus sequence to ensure efficient translation. The fidelity of the DNA encoding the glucagon-R and the GLP-1R was confirmed by DNA sequencing. The PCR products encoding the glucagon-R or the GLP-1R were subcloned into a mammalian expression vector containing a neomycin (G418) resistance marker.

The mammalian expression vectors encoding the glucagon-R or the GLP-1R were transfected into HEK293 cells by a standard calcium phosphate transfection method. 48 hr after transfection, cells were seeded for limited dilution cloning and selected with 1 mg/ml G418 in the culture medium. Three weeks later 12 surviving colonies of glucagon-R- and GLP-1R-expressing cells were picked, propagated and tested in the glucagon-R and GLP-1R efficacy assays as described below. One glucagon-R-expressing clone and one GLP-1R-expressing clone were chosen for compound profiling.

Glucagon Receptor and GLP-1 Receptor Efficacy Assays

HEK293 cells expressing the human glucagon-R or the human GLP-1R were seeded at 40,000 cells per well in 96-well microtiter plates coated with 0.01% poly-L-lysine, and grown for 1 day in culture in 100 μl growth medium. On the day of analysis, growth medium was removed and the cells were washed once with 200 μl Tyrode buffer. Cells were incubated in 100 μl Tyrode buffer containing increasing concentrations of test peptide (compound of the invention), 100 μM IBMX, and 6 mM glucose for 15 min at 37° C. The reaction was stopped by addition of 25 ml 0.5 M HCl and incubated on ice for 60 min. The cAMP content was estimated using the FlashPlate™ cAMP kit from Perkin-Elmer. EC$_{50}$ and relative efficacies compared to reference compounds (glucagon and GLP-1) were estimated by computer-assisted curve-fitting.

Results

EXAMPLE 1

Efficacy on GLP-1 and Glucagon Receptors

Efficacy of compounds of the invention was estimated by exposing cells expressing human glucagon-R and human GLP-1R to the compounds listed in Table 1 below at increasing concentrations and determining the cAMP formed, as described in the METHODS section, above.

EC$_{50}$ results for the compounds, together with corresponding values for human glucagon and human GLP-1 as reference compounds, are shown in Table 1:

TABLE 1

Efficacy (EC$_{50}$) of compounds of the invention at GLP-1 and glucagon receptors

| Sequence | Compound | EC$_{50}$ (nM) GLP-1R | EC$_{50}$ nM GluR |
|---|---|---|---|
| Glucagon | (ref. compd.) | 2.3 | 0.2 |
| GLP-1 | (ref. compd.) | 0 | 100000 |
| H-H-Aib-HGTFTSDYSKYLDS-K(hexadecanoyl-isoGlu)-AAHDFVEWLLSA-NH$_2$ (SEQ ID NO: 44) | Compound 1 | 0.21 | 0.26 |
| H-H-Aib-Q-DPhe-TFTSDYSKYLDS-K(hexadecanoyl-isoGlu)-AAHDFVEWLLSA-NH$_2$ (SEQ ID NO: 56) | Compound 2 | 0.88 | 1.1 |
| H-H-Aib-YGTFTSDYSKYLDS-K(hexadecanoyl-isoGlu)-AAHDFVEWLLSA-NH$_2$ (SEQ ID NO: 61) | Compound 3 | 0.48 | 1.4 |
| H-H-Aib-PGTFTSDYSKYLDS-K(hexadecanoyl-isoGlu)-AAHDFVEWLLSA-NH$_2$ (SEQ ID NO: 69) | Compound 4 | 0.10 | 0.48 |
| H-H-Aib-HGTFTSDYSKYLDS-K(hexadecanoyl-isoGlu)-AAHEFVEWLLEA-NH$_2$ (SEQ ID NO: 70) | Compound 5 | 0.16 | 0.15 |
| H-H-Aib-Q-DAla-TFTSDYSKYLDS-K(hexadecanoyl-isoGlu)-AAHDFVEWLLSA-NH$_2$ (SEQ ID NO: 72) | Compound 6 | 0.36 | 0.11 |
| H-H-Aib-EGTFTSDYSKYLDS-K(hexadecanoyl-isoGlu)-AAHDFVEWLLSA-NH$_2$ (SEQ ID NO: 43) | Compound 7 | 0.01 | 26 |
| H-H-Aib-QATFTSDYSKYLDS-K(hexadecanoyl-isoGlu)-AAHDFVEWLLSA-NH$_2$ (SEQ ID NO: 45) | Compound 8 | 8.2 | 3[a] |

TABLE 1-continued

Efficacy (EC$_{50}$) of compounds of the invention at GLP-1 and glucagon receptors

| Sequence | Compound | EC$_{50}$ (nM) GLP-1R | EC$_{50}$ nM) GluR |
|---|---|---|---|
| H-HSQ-Aib-TFTSDYSKYLDS-K(hexadecanoyl-isoGlu)-AAHDFVEWLLSA-NH$_2$ (SEQ ID NO: 49) | Compound 9 | 16 | 30 |
| H-H-Aib-QETFTSDYSKYLDS-K(hexadecanoyl-isoGlu)-AAHDFVEWLLSA-NH$_2$ (SEQ ID NO: 52) | Compound 10 | 20 | 15 |
| H-H-Aib-Q-Aib-TFTSDYSKYLDS-K(hexadecanoyl-isoGlu)-AAHDFVEWLLSA-NH$_2$ (SEQ ID NO: 53) | Compound 11 | 22 | 5.1 |
| H-H-Aib-QFTFTSDYSKYLDS-K(hexadecanoyl-isoGlu)-AAHDFVEWLLSA-NH$_2$ (SEQ ID NO: 54) | Compound 12 | 12 | 25 |
| H-H-Aib-LGTFTSDYSKYLDS-K(hexadecanoyl-isoGlu)-AAHDFVEWLLSA-NH$_2$ (SEQ ID NO: 58) | Compound 13 | 0.28 | 11 |
| H-H-Aib-Hph-GTFTSDYSKYLDS-K(hexadecanoyl-isoGlu)-AAHDFVEWLLSA-NH$_2$ (SEQ ID NO: 59) | Compound 14 | 3.5 | 8.9 |
| H-H-Aib-WGTFTSDYSKYLDS-K(hexadecanoyl-isoGlu)-AAHDFVEWLLSA-NH$_2$ (SEQ ID NO: 60) | Compound 15 | 5.8 | 43 |
| H-H-Aib-VGTFTSDYSKYLDS-K(hexadecanoyl-isoGlu)-AAHDFVEWLLSA-NH$_2$ (SEQ ID NO: 62) | Compound 16 | 0.13 | 3.0 |
| H-H-Aib-AGTFTSDYSKYLDS-K(hexadecanoyl-isoGlu)-AAHDFVEWLLSA-NH$_2$ (SEQ ID NO: 65) | Compound 17 | 0.09 | 3.4 |
| H-H-Aib-SGTFTSDYSKYLDS-K(hexadecanoyl-isoGlu)-AAHDFVEWLLSA-NH$_2$ (SEQ ID NO: 66) | Compound 18 | 0.09 | 8.0 |
| H-H-Aib-IGTFTSDYSKYLDS-K(hexadecanoyl-isoGlu)-AAHDFVEWLLSA-NH$_2$ (SEQ ID NO: 67) | Compound 19 | 0.16 | 0.74[b] |
| H-H-Aib-GGTFTSDYSKYLDS-K(hexadecanoyl-isoGlu)-AAHDFVEWLLSA-NH$_2$ (SEQ ID NO: 68) | Compound 20 | 0.21[c] | 26 |
| H-H-Aib-Cit-GTFTSDYSKYLDS-K(hexadecanoyl-isoGlu)-AAHDFVEWLLSA-NH$_2$ (SEQ ID NO: 71) | Compound 21 | 1.2 | 35 |
| H-H-Aib-[3-(2-furyl)alanyl]-GTFTSDYSKYLDS-K(hexadecanoyl-isoGlu)-AAHDFVEWLLSA-NH$_2$ (SEQ ID NO: 77) | Compound 22 | 0.06 | 3.8 |
| H-H-Aib-[3-(4-thiazolyl)-alanyl]-GTFTSDYSKYLDS-K(hexadecanoyl-isoGlu)-AAHDFVEWLLSA-NH$_2$ (SEQ ID NO: 78) | Compound 23 | 0.11 | 0.99 |
| H-H-Aib-[3-(3-pyridyl)-alanyl]-GTFTSDYSKYLDS-K(hexadecanoyl-isoGlu)-AAHDFVEWLLSA-NH$_2$ (SEQ ID NO: 79) | Compound 24 | 0.14 | 1.04 |
| H-H-Aib-[3-(1,2,4-triazol-1-yl)-alanyl]-GTFTSDYSKYLDS-K(hexadecanoyl-isoGlu)-AAHDFVEWLLSA-NH$_2$ (SEQ ID NO: 84) | Compound 25 | 0.09 | 0.71 |
| H-H-Aib-[3-(2-thienyl)-alanyl]-GTFTSDYSKYLDS-K(hexadecanoyl-isoGlu)-AAHDFVEWLLSA-NH$_2$ (SEQ ID NO: 81) | Compound 26 | 0.08 | 1.16 |
| H-H-Aib-[3-(3-thienyl)-alanyl]-GTFTSDYSKYLDS-K(hexadecanoyl-isoGlu)-AAHDFVEWLLSA-NH$_2$ (SEQ ID NO: 82) | Compound 27 | 0.27 | 1.58 |
| H-H-Aib-[3-(1-pyrazolyl)-alanyl]-GTFTSDYSKYLDS-K(hexadecanoyl-isoGlu)-AAHDFVEWLLSA-NH$_2$ (SEQ ID NO: 83) | Compound 28 | 0.11 | 4.85 |
| H-H-Aib-Hse-GTFTSDYSKYLDS-K(hexadecanoyl-isoGlu)-AAHDFVEWLLSA-NH$_2$ (SEQ ID NO: 73) | Compound 29 | 0.05 | 0.79 |
| H-H-Aib-Q-DLeu-TFTSDYSKYLDS-K(hexadecanoyl-isoGlu)-AAHDFVEWLLSA-NH$_2$ (SEQ ID NO: 74) | Compound 30 | 0.3 | 2.51 |
| H-H-Aib-HGTFTSDYSKYLES-K(hexadecanoyl-isoGlu)-AAEEFVEWLLEA-NH$_2$ (SEQ ID NO: 75) | Compound 31 | 0.09 | 0.15 |

[a] Redetermination relative to earlier determined value of 23.
[b] Redetermination relative to earlier determined value of 3.0.
[c] Redetermination relative to earlier determined value of 0.89.

The invention claimed is:

1. A compound having the formula:

$R^1$—Z—$R^2$, or a pharmaceutically acceptable salt thereof,
wherein
$R^1$ is H, $C_{1-4}$ alkyl, acetyl, formyl, benzoyl or trifluoroacetyl;
$R^2$ is OH or $NH_2$; and
Z is a peptide having the formula I:

H-Aib-HGTFTSDYSKYLES-K(hexadecanoyl-iso-Glu)-AAEEFVEWLLEA (SEQ ID NO:75).

2. The compound according to claim 1, wherein the compound is:

H-H-Aib-HGTFTSDYSKYLESK(hexadecanoyl-iso-Glu)-AAEEFVEWLLEA-$NH_2$ (SEQ ID NO:75).

3. A pharmaceutical composition comprising a compound according to claim 1, or a pharmaceutically acceptable salt thereof, together with a pharmaceutically acceptable carrier.

4. A method of promoting weight loss in a subject in need thereof, said method comprising administering to said subject a therapeutically effective amount of a compound according to claim 1.

5. A method of improving circulating glucose levels, glucose tolerance and/or circulating cholesterol levels, lowering circulating LDL levels, and/or increasing HDL/LDL ratio in a subject in need thereof, said method comprising administering to said subject a therapeutically effective amount of a compound according to claim 1.

6. A method of treating a condition caused by excess body weight in a subject in need thereof, said method comprising administering to said subject a therapeutically effective amount of a compound according to claim 1.

7. The method according to claim 5, wherein said compound is administered as part of a combination therapy together with an agent for treatment of diabetes, obesity, dyslipidaemia, or hypertension.

8. The method according to claim 7, wherein said agent for treatment of diabetes is metformin, a sulfonylurea, a glinide, a DPP-IV inhibitor, a glitazone, insulin, or an insulin analogue.

9. The method according to claim 7, wherein said agent for treatment of obesity is a glucagon-like peptide receptor 1 agonist, peptide YY or an analogue thereof, a cannabinoid receptor 1 antagonist, a lipase inhibitor, a melanocortin receptor 4 agonist, or a melanin concentrating hormone receptor 1 antagonist.

10. The method according to claim 7, wherein said agent for treatment of hypertension is an angiotensin-converting enzyme inhibitor, an angiotensin II receptor blocker, a diuretic, a beta-blocker, or a calcium channel blocker.

11. The method according to claim 7, wherein said agent for treatment of dyslipidaemia is a statin, a fibrate, a niacin, or a cholesterol absorption inhibitor.

12. The method according to claim 6, wherein said compound is administered as part of a combination therapy together with an agent for treatment of diabetes, obesity, dyslipidaemia, or hypertension.

13. The method according to claim 12, wherein said agent for treatment of diabetes is metformin, a sulfonylurea, a glinide, a DPP-IV inhibitor, a glitazone, insulin, or an insulin analogue.

14. The method according to claim 12, wherein said agent for treatment of obesity is a glucagon-like peptide receptor 1 agonist, peptide YY or an analogue thereof, a cannabinoid receptor 1 antagonist, a lipase inhibitor, a melanocortin receptor 4 agonist, or a melanin concentrating hormone receptor 1 antagonist.

15. The method according to claim 12, wherein said agent for treatment of hypertension is an angiotensin-converting enzyme inhibitor, an angiotensin II receptor blocker, a diuretic, a beta-blocker, or a calcium channel blocker.

16. The method according to claim 12, wherein said agent for treatment of dyslipidaemia is a statin, a fibrate, a niacin, or a cholesterol absorption inhibitor.

17. The method according to claim 6, wherein said condition caused by excess body weight is selected from the group consisting of: obesity, morbid obesity, obesity-linked inflammation, obesity-linked gallbladder disease, obesity-induced sleep apnea, pre-diabetes, insulin resistance, glucose intolerance, type 2 diabetes, type I diabetes, hypertension, atherogenic dyslipidaemia, atherosclerois, arteriosclerosis, coronary heart disease, peripheral artery disease, stroke, or microvascular disease.

* * * * *

SEQUENCE LISTING

<160> NUMBER OF SEQ ID NOS: 87

<210> SEQ ID NO 1
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 1

His Xaa Glu Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 2
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 2

His Xaa His Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 3
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 3

His Xaa Gln Ala Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 4
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 4

His Xaa Gln Val Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 5
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (4)..(4)
<223> OTHER INFORMATION: Xaa = Aib

<400> SEQUENCE: 5

His Gly Gln Xaa Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 6
<211> LENGTH: 29
<212> TYPE: PRT
<213> ORGANISM: Artificial
<220> FEATURE:
<223> OTHER INFORMATION: Synthetic peptide sequence

<400> SEQUENCE: 6

His Gly Glu Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 7
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (4)..(4)
<223> OTHER INFORMATION: Xaa = Aib

<400> SEQUENCE: 7

His Ser Gln Xaa Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 8
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 8

His Xaa Gln Leu Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 9
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 9

His Xaa Gln Pro Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 10
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 10

His Xaa Gln Glu Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 11
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (4)..(4)
<223> OTHER INFORMATION: Xaa = Aib

<400> SEQUENCE: 11

His Xaa Gln Xaa Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 12
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 12

His Xaa Gln Phe Thr Phe Thr Ser Asp Tyr Ser Lys Tyr Leu Asp Ser

```
                1               5                   10                  15
Lys Ala Ala His Asp Phe Val Glu Trp Leu Leu Ser Ala
            20                  25

<210> SEQ ID NO 13
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 13

His Xaa Phe Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 14
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (4)..(4)
<223> OTHER INFORMATION: Xaa = DPhe

<400> SEQUENCE: 14

His Xaa Gln Xaa Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 15
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 15

His Xaa Gln Arg Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 16
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
```

<223> OTHER INFORMATION: Xaa = Aib

<400> SEQUENCE: 16

His Xaa Leu Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 17
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Hph

<400> SEQUENCE: 17

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 18
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 18

His Xaa Trp Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 19
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 19

His Xaa Tyr Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 20
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE -continued
<222> LOCATION: (2)..(2)
<223> OTHER INFORMATION: Xaa = Aib

<400> SEQUENCE: 20

His Xaa Val Gly Thr Phe Thr Ser Asp Tyr Ser Lys Tyr Leu Asp Ser
1               5                   10                  15
Lys Ala Ala His Asp Phe Val Glu Trp Leu Leu Ser Ala
            20                  25

<210> SEQ ID NO 21
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 21

His Xaa Gln Lys Thr Phe Thr Ser Asp Tyr Ser Lys Tyr Leu Asp Ser
1               5                   10                  15
Lys Ala Ala His Asp Phe Val Glu Trp Leu Leu Ser Ala
            20                  25

<210> SEQ ID NO 22
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 22

His Xaa Arg Gly Thr Phe Thr Ser Asp Tyr Ser Lys Tyr Leu Asp Ser
1               5                   10                  15
Lys Ala Ala His Asp Phe Val Glu Trp Leu Leu Ser Ala
            20                  25

<210> SEQ ID NO 23
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 23

His Xaa Ala Gly Thr Phe Thr Ser Asp Tyr Ser Lys Tyr Leu Asp Ser
1               5                   10                  15
Lys Ala Ala His Asp Phe Val Glu Trp Leu Leu Ser Ala
            20                  25

<210> SEQ ID NO 24
<211> LENGTH: 29
<212> TYPE: PRT
<213> ORGANISM: Artificial
<220> FEATURE:
<223> OTHER INFORMATION: Synthetic peptide sequence
<220> FEATURE:

```
<221> NAME/KEY: MISC_FEATURE
<222> LOCATION: (2)..(2)
<223> OTHER INFORMATION: Xaa = Aib

<400> SEQUENCE: 24

His Xaa Ser Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 25
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 25

His Xaa Ile Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 26
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 26

His Xaa Gly Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 27
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 27

His Xaa Pro Gly Thr Phe Thr Ser Asp Tyr Ser Lys Tyr Leu Asp Ser
1               5                   10                  15

Lys Ala Ala His Asp Phe Val Glu Trp Leu Leu Ser Ala
            20                  25

<210> SEQ ID NO 28
<211> LENGTH: 29
<212> TYPE: PRT
<213> ORGANISM: Artificial
<220> FEATURE:
<223> OTHER INFORMATION: Synthetic peptide sequence
```

```
<220> FEATURE:
<221> NAME/KEY: MISC_FEATURE
<222> LOCATION: (2)..(2)
<223> OTHER INFORMATION: Xaa = Aib

<400> SEQUENCE: 28

His Xaa His Gly Thr Phe Thr Ser Asp Tyr Ser Lys Tyr Leu Asp Ser Lys
1               5                   10                  15

Ala Ala His Glu Phe Val Glu Trp Leu Leu Glu Ala
            20                  25

<210> SEQ ID NO 29
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Cit

<400> SEQUENCE: 29

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 30
<211> LENGTH: 27
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Q-DAla

<400> SEQUENCE: 30

His Xaa Thr Phe Thr Ser Asp Tyr Ser Lys Tyr Leu Asp Ser Lys Ala
1               5                   10                  15

Ala His Asp Phe Val Glu Trp Leu Leu Ser Ala
            20                  25

<210> SEQ ID NO 31
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Hse

<400> SEQUENCE: 31

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 32
<211> LENGTH: 27
<212> TYPE: PRT
<213> ORGANISM: Artificial
<220> FEATURE:
```

-continued

<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Q-DLeu

<400> SEQUENCE: 32

His Xaa Thr Phe Thr Ser Asp Tyr Ser Lys Tyr Leu Asp Ser Lys Ala
1               5                   10                  15

Ala His Asp Phe Val Glu Trp Leu Leu Ser Ala
            20                  25

<210> SEQ ID NO 33
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib

<400> SEQUENCE: 33

His Xaa His Gly Thr Phe Thr Ser Asp Tyr Ser Lys Tyr Leu Glu Ser
1               5                   10                  15

Lys Ala Ala Glu Glu Phe Val Glu Trp Leu Leu Glu Ala
            20                  25

<210> SEQ ID NO 34
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-1Nal

<400> SEQUENCE: 34

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 35
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(2-furyl)alanyl]

<400> SEQUENCE: 35

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 36
<211> LENGTH: 28
<212> TYPE: PRT
<213> ORGANISM: Artificial

-continued

```
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(4-thiazolyl)alanyl]

<400> SEQUENCE: 36

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 37
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(3-pyridyl)alanyl]

<400> SEQUENCE: 37

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 38
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(4-pyridyl)alanyl]

<400> SEQUENCE: 38

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 39
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(2-thienyl)alanyl]

<400> SEQUENCE: 39

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 40
<211> LENGTH: 28
<212> TYPE: PRT
```

```
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(3-thienyl)alanyl]

<400> SEQUENCE: 40

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 41
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(1-pyrazolyl)alanyl]

<400> SEQUENCE: 41

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 42
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(1,2,4-triazol-1-yl)alanyl]

<400> SEQUENCE: 42

His Xaa Gly Thr Phe Thr Ser Asp Tyr Ser Lys Tyr Leu Asp Ser Lys
1               5                   10                  15

Ala Ala His Asp Phe Val Glu Trp Leu Leu Ser Ala
            20                  25

<210> SEQ ID NO 43
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 43

His Xaa Glu Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30
```

```
<210> SEQ ID NO 44
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 44

His Xaa His Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 45
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 45

His Xaa Gln Ala Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 46
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 46

His Xaa Gln Val Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 47
<211> LENGTH: 30
<212> TYPE: PRT
<213> ORGANISM: Artificial
<220> FEATURE:
```

```
<223> OTHER INFORMATION: Synthetic peptide sequence
<220> FEATURE:
<221> NAME/KEY: MISC_FEATURE
<222> LOCATION: (4)..(4)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 47

His Gly Gln Xaa Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 48
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 48

His Gly Glu Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 49
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (4)..(4)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 49

His Ser Gln Xaa Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 50
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 50
```

```
His Xaa Gln Leu Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 51
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 51

His Xaa Gln Pro Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 52
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 52

His Xaa Gln Glu Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 53
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (4)..(4)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 53

His Xaa Gln Xaa Thr Phe Thr Ser Asp Tyr Ser Lys Tyr Leu Asp Ser
1               5                   10                  15
```

```
Lys Xaa Ala Ala His Asp Phe Val Glu Trp Leu Leu Ser Ala
        20                  25                  30
```

<210> SEQ ID NO 54
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 54

```
His Xaa Gln Phe Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
        20                  25                  30
```

<210> SEQ ID NO 55
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 55

```
His Xaa Phe Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
        20                  25                  30
```

<210> SEQ ID NO 56
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Q-DPhe
<220> FEATURE:
<221> NAME/KEY: MISC_FEATURE
<222> LOCATION: (16)..(16)
<223> OTHER INFORMATION: Xaa = (hexadecanoyl-isoGlu)

<400> SEQUENCE: 56

```
His Xaa Thr Phe Thr Ser Asp Tyr Ser Lys Tyr Leu Asp Ser Lys Xaa
1               5                   10                  15

Ala Ala His Asp Phe Val Glu Trp Leu Leu Ser Ala
        20                  25
```

<210> SEQ ID NO 57
<211> LENGTH: 30

```
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 57

His Xaa Gln Arg Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 58
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 58

His Xaa Leu Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 59
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Hph
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 59

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 60
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
```

<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 60

His Xaa Trp Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 61
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 61

His Xaa Tyr Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 62
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 62

His Xaa Val Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 63
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 63

His Xaa Gln Lys Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 64
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 64

His Xaa Arg Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 65
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 65

His Xaa Ala Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 66
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 66

His Xaa Ser Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

```
<210> SEQ ID NO 67
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 67

His Xaa Ile Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 68
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 68

His Xaa Gly Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 69
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 69

His Xaa Pro Gly Thr Phe Thr Ser Asp Tyr Ser Lys Tyr Leu Asp Ser
1               5                   10                  15

Lys Xaa Ala Ala His Asp Phe Val Glu Trp Leu Leu Ser Ala
            20                  25                  30

<210> SEQ ID NO 70
<211> LENGTH: 30
<212> TYPE: PRT
<213> ORGANISM: Artificial
<220> FEATURE:
<223> OTHER INFORMATION: Synthetic peptide sequence
```

```
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 70

His Xaa His Gly Thr Phe Thr Ser Asp Tyr Ser Lys Tyr Leu Asp Ser
1               5                   10                  15

Lys Xaa Ala Ala His Glu Phe Val Glu Trp Leu Leu Glu Ala
            20                  25                  30

<210> SEQ ID NO 71
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Cit
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 71

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 72
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Q-DAla
<220> FEATURE:
<221> NAME/KEY: MISC_FEATURE
<222> LOCATION: (16)..(16)
<223> OTHER INFORMATION: Xaa = (hexadecanoyl-isoGlu)

<400> SEQUENCE: 72

His Xaa Thr Phe Thr Ser Asp Tyr Ser Lys Tyr Leu Asp Ser Lys Xaa
1               5                   10                  15

Ala Ala His Asp Phe Val Glu Trp Leu Leu Ser Ala
            20                  25

<210> SEQ ID NO 73
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Hse
<220> FEATURE:
<221> NAME/KEY: MISC_FEATURE
<222> LOCATION: (17)..(17)
```

<223> OTHER INFORMATION: Xaa = (hexadecanoyl-isoGlu)

<400> SEQUENCE: 73

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 74
<211> LENGTH: 28
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-Q-DLeu
<220> FEATURE:
<221> NAME/KEY: MISC_FEATURE
<222> LOCATION: (16)..(16)
<223> OTHER INFORMATION: Xaa = (hexadecanoyl-isoGlu)

<400> SEQUENCE: 74

His Xaa Thr Phe Thr Ser Asp Tyr Ser Lys Tyr Leu Asp Ser Lys Xaa
1               5                   10                  15

Ala Ala His Asp Phe Val Glu Trp Leu Leu Ser Ala
            20                  25

<210> SEQ ID NO 75
<211> LENGTH: 30
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib
<220> FEATURE:
<221> NAME/KEY: MISC_FEATURE
<222> LOCATION: (18)..(18)
<223> OTHER INFORMATION: Xaa = (hexadecanoyl-isoGlu)

<400> SEQUENCE: 75

His Xaa His Gly Thr Phe Thr Ser Asp Tyr Ser Lys Tyr Leu Glu Ser
1               5                   10                  15

Lys Xaa Ala Ala Glu Glu Phe Val Glu Trp Leu Leu Glu Ala
            20                  25                  30

<210> SEQ ID NO 76
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-1Nal
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 76

His Xaa Gly Thr Phe Thr Ser Asp Tyr Ser Lys Tyr Leu Asp Ser Lys
1               5                   10                  15

```
<210> SEQ ID NO 77
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(2-furyl)alanyl]
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 77

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 78
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(4-thiazolyl)alanyl]
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 78

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 79
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(3-pyridyl)alanyl]
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 79

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 80
<211> LENGTH: 29
<212> TYPE: PRT
```

```
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(4-pyridyl)alanyl]
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 80

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 81
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(2-thienyl)alanyl]
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 81

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 82
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(3-thienyl)alanyl]
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 82

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 83
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(1-pyrazolyl)alanyl]
```

```
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 83

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 84
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib-[3-(1,2,4-triazol-1-yl)alanyl]
<220> FEATURE:
<221> NAME/KEY: MISC_FEATURE
<222> LOCATION: (17)..(17)
<223> OTHER INFORMATION: Xaa = (hexadecanoyl-isoGlu)

<400> SEQUENCE: 84

His Xaa Gly Thr Phe Thr Ser Asp Tyr Ser Lys Tyr Leu Asp Ser Lys
1               5                   10                  15

Xaa Ala Ala His Asp Phe Val Glu Trp Leu Leu Ser Ala
            20                  25

<210> SEQ ID NO 85
<211> LENGTH: 29
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (2)..(2)
<223> OTHER INFORMATION: Xaa = Aib, Ser or Gly
<220> FEATURE:
<221> NAME/KEY: MISC_FEATURE
<222> LOCATION: (3)..(3)
<223> OTHER INFORMATION: Xaa = Gln, Glu, Gly, His, Phe, Leu, Trp, Tyr,
      Val, Arg, Ala, Ser, Ile, Pro, Hph, Hse, Cit, 1-Nal or
      3-(heterocyclyl)alanine
<220> FEATURE:
<221> NAME/KEY: MISC_FEATURE
<222> LOCATION: (4)..(4)
<223> OTHER INFORMATION: Xaa = Gly, Ala, D-Ala, Val, Aib, Leu, D-Leu,
      Pro, Glu, Phe, D-Phe, Arg or Lys
<220> FEATURE:
<221> NAME/KEY: MISC_FEATURE
<222> LOCATION: (15)..(15)
<223> OTHER INFORMATION: Xaa = Asp or Glu
<220> FEATURE:
<221> NAME/KEY: MISC_FEATURE
<222> LOCATION: (17)..(17)
<223> OTHER INFORMATION: Xaa = Arg or X
<220> FEATURE:
<221> NAME/KEY: MISC_FEATURE
<222> LOCATION: (20)..(20)
<223> OTHER INFORMATION: Xaa = Arg, His or X
<220> FEATURE:
<221> NAME/KEY: MISC_FEATURE
<222> LOCATION: (21)..(21)
<223> OTHER INFORMATION: Xaa = Asp or Glu
<220> FEATURE:
<221> NAME/KEY: MISC_FEATURE
<222> LOCATION: (24)..(24)
<223> OTHER INFORMATION: Xaa = Ala or X
```

```
<220> FEATURE:
<221> NAME/KEY: MISC_FEATURE
<222> LOCATION: (27)..(27)
<223> OTHER INFORMATION: Xaa = Leu or X
<220> FEATURE:
<221> NAME/KEY: MISC_FEATURE
<222> LOCATION: (28)..(28)
<223> OTHER INFORMATION: Xaa = Arg or X, wherein each residue X is
      independently selected from the group consisting of Glu, Lys, Ser,
      Cys, Dbu, Dpr and Orn

<400> SEQUENCE: 85

His Xaa Xaa Xaa Thr Phe Thr Ser Asp Tyr Ser Lys Tyr Leu Xaa Ser
1               5                   10                  15

Xaa Ala Ala Xaa Xaa Phe Val Xaa Trp Leu Xaa Xaa Ala
            20                  25

<210> SEQ ID NO 86
<211> LENGTH: 29
<212> TYPE: PRT
<213> ORGANISM: Artificial
<220> FEATURE:
<223> OTHER INFORMATION: Synthetic peptide sequence

<400> SEQUENCE: 86

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 87
<211> LENGTH: 37
<212> TYPE: PRT
<213> ORGANISM: Artificial
<220> FEATURE:
<223> OTHER INFORMATION: Synthetic peptide sequence

<400> SEQUENCE: 87

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35
```